(12) United States Patent
Gelbin et al.

(10) Patent No.: US 7,947,769 B2
(45) Date of Patent: May 24, 2011

(54) LIQUID AMYLARYL PHOSPHITE COMPOSITIONS AND ALKYLATE COMPOSITIONS FOR MANUFACTURING SAME

(75) Inventors: Michael E. Gelbin, Middlebury, CT (US); Maurice Power, Manchester (GB); Jonathan Hill, Manchester (GB)

(73) Assignee: Chemtura Corporation, Middlebury, CT (US)

(*) Notice: Subject to any disclaimer, the term of this patent is extended or adjusted under 35 U.S.C. 154(b) by 0 days.

(21) Appl. No.: 12/534,019

(22) Filed: Jul. 31, 2009

(65) Prior Publication Data

US 2010/0069542 A1  Mar. 18, 2010

Related U.S. Application Data

(63) Continuation-in-part of application No. 11/787,531, filed on Apr. 16, 2007.

(60) Provisional application No. 60/815,819, filed on Jun. 20, 2006.

(51) Int. Cl.
*C08K 5/51* (2006.01)

(52) U.S. Cl. ...................................... 524/128

(58) Field of Classification Search .................. 524/128
See application file for complete search history.

(56) References Cited

U.S. PATENT DOCUMENTS

| | | | |
|---|---|---|---|
| 2,220,845 A | 11/1940 | Moyle |
| 2,834,798 A | 5/1958 | Hechenbleikner et al. |
| 3,412,064 A | 11/1968 | Brindell |
| 3,492,377 A | 1/1970 | Kline |
| 3,558,554 A | 1/1971 | Kuriyama et al. |
| 3,644,536 A | 2/1972 | Bafford |
| 3,755,200 A | 8/1973 | Rhodes et al. |
| 3,756,906 A | 9/1973 | Nicholas et al. |
| 3,787,537 A | 1/1974 | De Marcq |
| 4,261,880 A | 4/1981 | Fujii et al. |
| 4,276,233 A | 6/1981 | Markezich et al. |
| 4,321,218 A | 3/1982 | Rasberger et al. |
| 4,383,950 A | 5/1983 | Rasberger |
| 4,406,842 A | 9/1983 | Spivack |
| 4,492,661 A | 1/1985 | Maul et al. |
| 4,829,112 A | 5/1989 | Ishii et al. |
| 5,208,368 A | 5/1993 | Scherzer et al. |
| 5,254,610 A | 10/1993 | Small, Jr. et al. |
| 5,254,709 A | 10/1993 | Hunter |
| 5,322,871 A | 6/1994 | Pitteloud et al. |
| 5,401,845 A | 3/1995 | Pitteloud et al. |
| 5,532,401 A | 7/1996 | Stevenson et al. |
| 5,561,181 A | 10/1996 | Mahood |
| 6,576,788 B1 | 6/2003 | Penzel et al. |
| 6,824,711 B2 | 11/2004 | Stevenson et al. |
| 6,846,859 B2 | 1/2005 | Coffy et al. |
| 6,887,926 B1 | 5/2005 | Parhar et al. |
| 7,157,511 B2 | 1/2007 | Bobsein et al. |
| 7,176,252 B2 | 2/2007 | Stevenson et al. |
| 7,320,764 B2 | 1/2008 | Stevenson et al. |
| 7,361,703 B2 | 4/2008 | Tikuisis et al. |
| 7,468,410 B2 | 12/2008 | Chafin et al. |
| 2003/0078340 A1 | 4/2003 | Fatnes et al. |
| 2004/0048958 A1 | 3/2004 | Didier |
| 2007/0149660 A1 | 6/2007 | Kumar et al. |
| 2007/0228343 A1 | 10/2007 | Roth et al. |

FOREIGN PATENT DOCUMENTS

| | | |
|---|---|---|
| DE | 2940620 | 4/1981 |
| EP | 0 090 524 | 10/1983 |
| EP | 0 245 852 | 11/1987 |
| EP | 0551 062 | 7/1993 |
| GB | 1 298 248 | 11/1972 |
| GB | 2 227 490 | 8/1990 |
| JP | 7 309884 | 11/1995 |
| RU | 2 140 938 | 11/1999 |
| WO | 2007/149143 | 12/2007 |

OTHER PUBLICATIONS

U.S. Appl. No. 12/534,000.*
U.S. Appl. No. 12/534,035.*
U.S. Appl. No. 12/534,000, Gelbin et al., filed Jul. 31, 2009.*
U.S. Appl. No. 12/534035, Gelbin et al., filed Jul. 31, 2009.*
International Search Report mailed Dec. 6, 2007; of PCT Application No. PCT/US2007/009690; 3 pgs.
International Preliminary Report on Patentability mailed Dec. 22, 2008; of PCT Application No. PCT/US2007/009690; 6 pgs.

* cited by examiner

*Primary Examiner* — Ling-Siu Choi
*Assistant Examiner* — Sonya Wright
(74) *Attorney, Agent, or Firm* — Joseph Suhadolnik

(57) ABSTRACT

Alkylate compositions comprising a monoamylphenol in an amount ranging from 25 weight percent to 99 weight percent and a diamylphenol in an amount ranging from 1 weight percent to 60 weight percent, the weight percentages being based on the total weight of all components in the alkylate composition. The invention is also to processes for making such alkylate compositions and to processes for forming stable liquid amylaryl phosphite compositions from such alkylate compositions.

13 Claims, No Drawings

LIQUID AMYLARYL PHOSPHITE COMPOSITIONS AND ALKYLATE COMPOSITIONS FOR MANUFACTURING SAME

CROSS REFERENCE TO RELATED APPLICATION(S)

This application is a continuation-in-part of U.S. patent application Ser. No. 11/787,531, filed Apr. 16, 2007, which claims priority to U.S. Provisional Application No. 60/815,819, filed Jun. 20, 2006. Each of these applications is incorporated herein by reference in its entirety.

FIELD OF INVENTION

The present invention relates to novel amylaryl phosphite compositions and to alkylate compositions for making same. More specifically, the invention relates to novel compositions of amylated phenolic compounds that are useful, for example, in producing liquid amylaryl phosphite compositions. The resultant amylaryl phosphite compositions are liquid at ambient conditions and may be used, for example, to stabilize polyolefin resin compositions.

BACKGROUND OF THE INVENTION

Stabilizers are often used in polymeric compositions, e.g., polyolefins, polyvinyl halides, polyesters, polyamides, nitrile polymers, styrenic polymers and acrylate polymers and elastomeric materials such as butadiene rubber, polyisoprene etc to stabilize the polymeric compositions against the effects of heat and light degradation. Exemplary of such stabilizers are phenolic antioxidants, hindered amine light stabilizers, ultraviolet light absorbers, phosphite antioxidants, metal salts of fatty acids, hydrotalcites, metal oxides, epoxidized oils, hydroxylamines, amine oxides, lactones, and thiosynergists. In particular, organic phosphites have been used as antioxidants, e.g., secondary antioxidants, for polyolefins, polyvinyl chloride, and elastomers. Examples of such phosphites are disclosed in H. Zweifel (Ed) Plastics Additives Handbook, 5th edition, Hanser Publishers, Munich 2000.

Phosphite stabilizers, both liquid and solid, are known in the art. Many of the most effective organic phosphites are solids at ambient temperature and accordingly do not lend themselves to being processed with certain polymers, and in particular, with low melting point polymers. Owing to their solid form and concomitant processing limitations, for example, some solid alkylaryl phosphites have been demonstrated to plateout during processing in some plastics, in particular low melting point plastics, and form deposits on processing machinery surfaces. In addition, solid organic phosphites typically must be processed, e.g., heated and melted, in order to be incorporated into the respective polymer compositions thereby increasing handling and processing costs.

One of the most widely used solid organic phosphites is tris(2,4-di-t-butylphenyl)phosphite, which is commercially sold under the trade name Alkanox® 240 (Chemtura Corporation, Middlebury, Conn., USA). Tris(2,4-di-t-butylphenyl) phosphite has some processability and solubility limitations, however, owing to its solid form. U.S. Pat. No. 5,254,709, the entirety of which is incorporated herein by reference, describes the synthesis of tris(2,4-di-tert-butyl)phenyl phosphite by reacting an alkylated phenol intermediate, i.e., 2,4-di-tert-butyl phenol, with phosphorus trichloride in the presence of catalyst according to the following reaction:

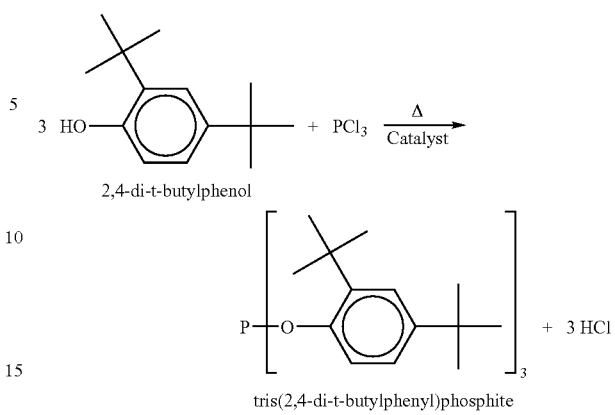

Liquid phosphite compositions are also well known and do not possess the handling problems associated with solid phosphite compounds. In addition, liquid phosphite compositions generally exhibit better processability than solid phosphite compositions for polymers that process at low temperatures. Tris(p-nonylphenyl)phosphite (TNPP), for example, is one alkylaryl phosphite that is a stable liquid at ambient conditions.

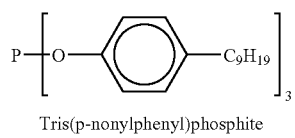

Tris(p-nonylphenyl)phosphite

TNPP is a versatile phosphite stabilizer that is useful in stabilizing a large number of polymers such as HDPE, LLDPE, SBR, ABS, PVC and others. There is, however, a need to replace TNPP owing to the alleged estrogenicity of nonylphenol, which is used in the manufacture of TNPP.

Thus, the need exists for novel alkylaryl phosphite compositions that are liquids at ambient conditions while not having the perceived estrogenicity concerns associated with nonylphenol and having the ability to effectively stabilize polymer resins and compositions against heat and light degradation. The need also exists for methods for producing such phosphite stabilizers, to novel alkylated phenolic intermediates for forming such phosphite stabilizers, and to processes for forming such novel alkylated phenolic compositions.

SUMMARY OF THE INVENTION

The present invention, in one embodiment, is directed to an alkylate composition that is useful, for example, in producing a phosphite composition that may be utilized to stabilize polymer compositions. In one embodiment, the alkylate composition comprises a monoamylphenol and a diamylphenol. Preferably, the monoamylphenol is present in an amount ranging from 25 weight percent to 99 weight percent and the diamylphenol is present in an amount ranging from 1 weight percent to 60 weight percent. Additionally, the ratio of monoamylphenol to diamylphenol may range from 5:1 to 1:2. In one embodiment, the amyl substituents are tert-amyl groups.

In another embodiment, the invention relates to a method for forming the above-identified alkylate composition. The inventive method comprises contacting one or more amylenes with a phenol at a molar ratio ranging from 1:1 to 6:1, optionally in the presence of a catalyst, and under conditions effective to form the alkylate composition. In another embodiment, the amylenes and the phenols are selected so as to produce a target alkylate composition. Preferably, the resultant alkylate composition is substantially colorless and contains less than 4 weight percent tri-alkylaryl, e.g., tri-alkylphenol, compounds and less than 4 weight percent residual non-amylated phenols.

In addition, in another embodiment, the invention relates to a method for forming the phosphite composition discussed above. The method comprises reacting a phosphorus trihalide with the alkylate composition to form the phosphite composition. Thus, in another embodiment, the invention further relates to the phosphite composition that may be produced via the inventive method. Preferably, the phosphite composition is a liquid at ambient conditions and comprises at least two of a tris(diamylaryl)phosphite, a tris(monoamylaryl)phosphite, a bis(diamylaryl)monoamylaryl phosphite, and a bis(monoamylaryl)diamylaryl phosphite. In addition, the invention also relates to a polymeric composition comprising a polymeric resin and the phosphite composition.

DETAILED DESCRIPTION OF THE INVENTION

Introduction

The present invention relates to the formation of liquid alkyaryl phosphite compositions from novel alkylate compositions, which comprise a plurality of alkylated phenols, specifically two or more amylated phenols. In a preferred embodiment, the alkylate composition comprises at least one monoamylphenol and at least one diamylphenol, with the monoamylphenols present in an amount ranging from 25 to 99 wt % and the diamylphenols being present in an amount ranging from 1 to 60 wt %. The invention also relates to methods for forming the alkylate compositions and to methods for reacting alkylate composition with a phosphorous halide to form a liquid amylaryl phosphite composition. It has now been discovered that only certain alkylate compositions, e.g., those having certain weight ratios of monoamylphenols to diamylphenols, may be suited for being reacted with a phosphorous halide to form an amylaryl phosphite composition that is a liquid at ambient conditions. By "ambient conditions" it is meant room temperature, e.g., 25° C., and 1 atmosphere pressure.

In one embodiment, the present invention relates to an alkylate composition comprising a composition of at least two different amylphenols, meaning phenols that are substituted with at least one amyl group, e.g., a tert-amyl group. As used herein, the terms "phenol" and "phenolic" are used to refer to any compound that contains a six member aromatic ring, bonded directly to a hydroxyl group (—OH), and includes, for example, hydroxybenzene, cresol, e.g., o-, m- and/or p-cresol, xylenol, and various mixtures thereof. The term "amyl" and "amyl group" means any $C_5$-containing substituent. Examples of amyl groups include n-amyl, iso-amyl, tert-amyl, sec-amyl, neo-amyl, 2-methyl-1-butyl, 3-methyl-2-butyl, or 3-amyl.

As indicated above, the alkylate composition comprises at least two different amylated phenols, e.g., at least three, or at least four different amylphenols, selected from monoamylphenols and diamylphenols. The alkylate composition optionally further comprises one or more triamylphenols. Thus, the alkylate composition comprises at least one phenolic that is multiply substituted, e.g., diamylphenol such as 2,4-di-tert-amylphenol, and at least one phenolic that is monosubstituted, e.g., a monoamylphenol such as 4-tert-amylphenol. Preferably, the alkylate composition does not contain exclusively monoamylphenols or exclusively diamylphenols.

In a preferred embodiment, the at least one monoamylphenol comprises a para-monoamylphenol of structure (I) and the diamylphenol is a 2,4-diamylphenol of structure (II):

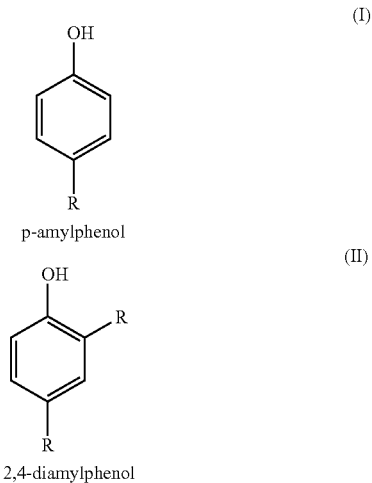

wherein R represents the same or different amyl group, e.g., n-amyl, iso-amyl, tert-amyl, sec-amyl, neo-amyl, 3-amyl, 3-methyl-2-butyl, or 2-methyl-1-butyl. In some embodiments, the alkylate composition may comprise more than one monoamylphenol and/or more than one diamylphenol. For example, the alkylate composition may comprise p-amylphenol of formula (I), o-amylphenol (not shown) and 2,4-diamylphenol of formula (II).

Alkylate Compositions

In some embodiments, the alkylate composition comprises one or more amylphenols that are alkylated exclusively with amyl substituents. That is, the alkylate composition does not contain any non-amylphenols. By "non-amylphenols," it is meant any phenol in which the phenolic moiety is unsubstituted or, if substituted, is substituted exclusively with one or more alkyl groups other than amyl.

In other embodiments, however, the alkylate composition may comprise one or more non-amylphenols in addition to the amylphenols. If the alkylate composition comprises any non-amylphenols, then the non-amyl substituent may comprise, for example, one or more $C_1$-$C_{18}$, e.g., $C_4$-$C_{10}$, alkyl groups other than amyl. In this aspect, the non-amyl alkyl substituent(s) on the phenol moiety may be selected from straight-chain or branched $C_1$-$C_{18}$ alkyl, e.g., $C_1$-$C_{10}$ alkyl, $C_1$-$C_8$ alkyl, $C_4$-$C_{10}$ alkyl, $C_4$-$C_6$ alkyl or $C_4$ alkyl ("butyl" groups), other than amyl. The one or more non-amyl substituents may include, for example, one or more of methyl, ethyl, propyl, butyl (especially sec-butyl, iso-butyl, and/or tert-butyl), hexyl, heptyl, octyl, nonyl (although less preferred), decyl, undecyl, dodecyl, tridecyl, tetradecyl, pentadecyl, hexadecyl, heptadecyl, octadecyl, and isomers thereof. If the alkylate composition further comprises one or more non-amylphenols, it optionally comprises the non-amylphenol(s) in an amount less than 5 wt %, e.g., less than 3 wt % or less than 1 wt %, optionally from 0 to 5 wt %, from 0.5 to 3 wt % or from 0.5 to 1.5 wt %. As such, in one embodiment, the monoamylphenols and the diamylphenols, combined, are present in an amount greater than 80 wt %, e.g., greater than 90 wt %, greater than 95 wt %, or greater than 97 wt %.

Optionally, the alkylate composition may comprise greater amounts of non-amylphenols, e.g., on the order of from 0 to 20 wt % non-amylphenols, from 1 to 10 wt % non-amylphenols, or from 1 to 5 wt % non-amylphenols, based on the total weight of all phenolics in the alkylate composition.

In a preferred embodiment, the phosphite composition is substantially free of $C_8$-$C_{10}$ alkyl groups. In preferred embodiments, the alkyl moieties do not include nonyl, meaning the phosphite composition preferably comprises less than 50 wppm, e.g., less than 10 wppm or less than 5 wppm nonyl substituted aryl phosphite compounds, and most preferably no detectable nonyl substituted aryl phosphite compounds. In addition, the phosphite composition is substantially free of nonyl/aryl preferably comprises less than 50 wppm, e.g., less than 10 wppm or less than 5 wppm nonylphenol, and most preferably no detectable nonylphenol. The term "wppm" refers to parts per million based on the total weight of the phosphite composition.

In one embodiment, a majority of the alkylphenols in the alkylate composition and preferably substantially all of the alkylphenols in the alkylate compositions, e.g., at least 90 wt %, at least 95 wt %, or at least 99 wt % of the alkylphenols in the alkylate compositions, are amylphenols, meaning they are substituted with at least one amyl group. As indicated above, the amyl groups may be straight chain amyl groups and/or branched amyl groups. Examples of preferred amyl groups include n-amyl, iso-amyl, tert-amyl, sec-amyl, neo-amyl, 3-amyl, 3-methyl-2-butyl, or 2-methyl-1-butyl. In a preferred embodiment, at least 90 wt %, e.g., at least 95 wt %, at least 98 wt % or at least 99 wt % of the amylphenols are substituted with one or more tert-amyl groups. Similarly, in a preferred embodiment, at least 90 wt %, e.g., at least 95 wt %, at least 98 wt % or at least 99 wt % of the amyl substituents in the alkylate composition are tert-amyl substituents.

As indicated above, in one embodiment, the alkylate composition comprises at least one monoamylphenol and at least one diamylphenol. Where the phenolic is hydroxybenzene, the alkylate compositions may comprise one or more monoamylphenols of structures (III)-(V):

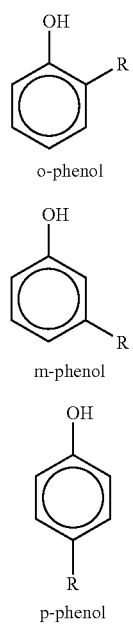

wherein R is an amyl group, e.g., n-amyl, tert-amyl, neo-amyl, iso-amyl, sec-amyl, 2-methyl-1-butyl, 3-methyl-2-butyl, or 3-amyl, preferably tert-amyl. In one embodiment, the monoamylphenol is selected from the group consisting of 4-tert-amylphenol, 2-tert-amylphenol, and 4-sec-amylphenol, with 4-tert-amylphenol being preferred.

Similarly, where the aryl moiety is hydroxybenzene, the alkylate compositions may comprise the diamylphenol, 2,4-diamylphenol, of structure (II), above, wherein R is an amyl group, e.g., n-amyl, tert-amyl, neo-amyl, iso-amyl, sec-amyl, 2-methyl-1-butyl, 3-methyl-2-butyl, or 3-amyl, preferably tert-amyl. The two amyl groups in a given diamylphenol compound may be of the same type or different from one another. For example, both amyl groups may be tert-amyl, or one amyl group may be tert-amyl and the other amyl group may be sec-amyl.

As indicated above, the alkylate composition optionally further comprises one or more triamylphenols, e.g., triamyl-hydroxybenzene or triamyl-o-cresol, in which the phenol is substituted with three amyl groups, the same or different, e.g., one or more of n-amyl, tert-amyl, neo-amyl, iso-amyl, sec-amyl, 2-methyl-1-butyl, 3-methyl-2-butyl, or 3-amyl, preferably tert-amyl. For example, if the phenolic moiety is hydroxybenzene, the triamylphenol may be substituted in the two ortho positions and in the para position of the phenyl group.

For monoamylphenols, the amyl group preferably is substituted on one of the 2-position, 4-position, or the 6-position of the phenolic moiety, although meta substitutions (3- and/or 5-positions) are also contemplated. It is also contemplated that the alkylate compositions may comprise multiple monoamylphenols, each being substituted in different positions. For diamylphenols, the amyl groups preferably substitute the phenolic moiety in the 2- and 4-positions as shown in structure (II) above, although substitution in the 2- and 6-positions is also possible. For triamylphenols, the amyl groups preferably substitute the phenolic moiety in the 2-, 4-, and 6-positions.

In one embodiment, the amylphenols in the alkylate composition are independently selected phenolics of structure (VI):

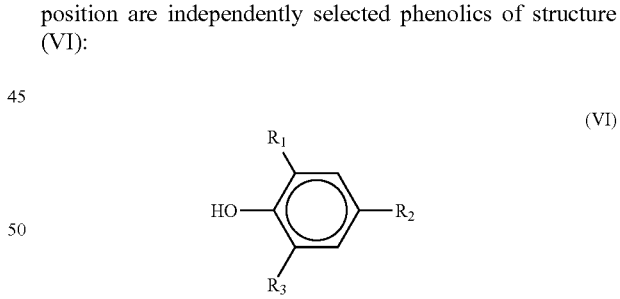

wherein $R_1$, $R_2$, and $R_3$ are independently selected from the group consisting of hydrogen and $C_1$-$C_8$ alkyl, e.g., methyl, ethyl, propyl, butyl, amyl, hexyl, heptyl, octyl, and isomers thereof, e.g., isopropyl, tert-butyl, tert-amyl, neo-amyl, preferably amyl and its isomers, provided that at least one of $R_1$, $R_2$, and $R_3$ is an amyl group, e.g., n-amyl, t-amyl, neo-amyl, iso-amyl, sec-amyl, 2-methyl-1-butyl, 3-methyl-2-butyl, or 3-amyl. In a preferred embodiment, $R_1$ and $R_3$ are hydrogen, and $R_2$ is an amyl group for at least some of the amylphenol compounds in the alkylate composition, as shown in structure (V) above. Additionally, the alkylate composition preferably comprises at least some amylated phenol compounds in which the ortho and para positions, e.g., $R_2$ and $R_3$, are amyl groups and $R_1$ is hydrogen, as shown in structure (II) above. Preferably, the amyl groups have no α-hydrogen atoms, i.e., are tert-amyl.

In one embodiment, the alkylate composition comprises independently selected phenolics of the structure (VII):

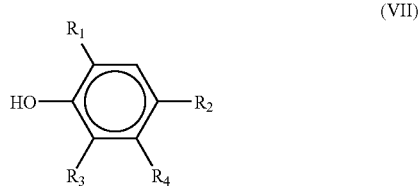

(VII)

wherein $R_1$, $R_2$, and $R_3$ are defined above and $R_4$ is hydrogen or methyl, provided that one of $R_1$, $R_2$, $R_3$, and $R_4$ is methyl and that at least two of $R_1$, $R_2$, $R_3$, and $R_4$ are not hydrogen. Cresols are exemplary of such phenols.

In preferred embodiments, the alkylate composition comprises a monoamyl phenol, e.g., a 4-amylphenol and a diamylphenol, e.g., a 2,4-di-amylphenol. The 4-amylphenol optionally is present in an amount greater than 40 wt %, greater than 50 wt %, greater than 60 wt %, greater than 70 wt % or greater than 75 wt %. The 4-amylphenol optionally is present in an amount less than 95 wt %, e.g., less than 85 wt %, less than 80 wt %, less than 75 wt % or less than 65 wt %. In terms of ranges, in some embodiments, the 4-amylphenol, e.g., 4-tert-amylphenol, is present in an amount ranging from 25 wt % to 99 wt %, e.g., from 45 wt % to 80 wt %, from 60 wt % to 75 wt %, or from 65 wt % to 75 wt %. In this aspect, the diamylphenols, e.g., 2,4-di-tert-amylphenol, preferably are present in an amount ranging from 1 wt % to 60 wt %, e.g., from 10 wt % to 50 wt %, from 25 wt % to 40 wt %, or from 25 wt % to 35 wt %. Optionally, the diamylphenol is present in an amount less than 60 wt %, e.g., less than 55 wt %, less than 45 wt % or less than 35 wt %. In terms of lower range limitations, the diamylphenol, e.g., 2,4-di-tert-amylphenol, optionally is present in an amount greater than 10 wt %, greater than 20 wt %, greater than 30 wt %, or greater than 40 wt %.

The weight ratio of monoamylphenols, such as 4-tert-amylphenol, to diamylphenols, e.g., 2,4-di-tert-amylphenol, can be selected or adjusted so as to produce the desired alkylate composition that is suitable for being used as a reactant for forming an alkylaryl phosphite composition that is a liquid at ambient conditions. Preferably, the weight ratio of monoamylphenols to diamylphenols in the alkylate compositions ranges from 5:1 to 1:2, e.g., from 5:1 to 1:1.5, from 3:1 to 1:1, or from 1.5:1 to 1:1. Alkylate compositions outside of these weight ratio ranges may produce phosphite compositions that are not liquids and/or are meta-stable liquids under ambient conditions.

In one embodiment, a majority of the phenol moieties are mono substituted in the para-position, e.g., at least 50%, at least 70%, or at least 90% mono substituted in the para-position, optionally from 50 to 95%, e.g., from 55 to 90 or from 60 to 85% mono substituted in the para-position, based on the number of phenol moieties in the alkylate composition. In addition, some of the phenol moieties are disubstituted, e.g., ortho- and para-disubstituted, at least in part. Preferably at least 10% of the phenol moieties are ortho- and para-disubstituted, e.g., at least 20% ortho- and para-disubstituted, or at least 50% ortho- and para-disubstituted, optionally from 5 to 50% ortho- and para-disubstituted, e.g., from 10 to 45%, or from 15 to 40% ortho- and para-disubstituted, based on the total number of phenol moieties in the phosphite composition. In other embodiments, the ratio of monosubstituted groups to disubstituted groups ranges from 5:1 to 1:1, e.g., from 4:1 to 1:1, or from 3.5:1 to 2:1.

The utilization of the above-described ratios and weight percentages provide alkylate compositions that are capable of producing phosphite compositions, when reacted with a phosphorous halide, that are stable liquids and have relatively low viscosities, e.g., less than 10,000 cSt, less than 7,500 cSt, less than 5,000 cSt, or less than 3,000 cSt, as measured at 30° C. Also, the resultant phosphite compositions are stable and are not meta-stable, meaning that the phosphite compositions remain liquid after three freeze/thaw cycles. Other alkylate composition compositions, e.g., alkylate compositions comprising greater than 90 wt % of 4-amylphenol, may produce phosphite compositions that are not liquids and/or are meta-stable liquids under ambient conditions. Thus, by adjusting the percentages of the components of the alkylate compositions and/or the ratio of these components as indicated above, alkylate compositions that produce stable low viscosity liquid phosphite compositions may be achieved. Of course, other factors, e.g., phenolic excess, reaction temperature profile, final residual phenolic content, etc., can also impact the resultant phosphite compositions.

The alkylate composition optionally further comprises one or more of a 2-amylphenol and/or a triamylphenol. If the alkylate composition further comprises 2-amylphenol, it preferably comprises the 2-amylphenol in an amount less than 4 wt %, e.g., less than 2 wt %, less than 1 wt %, less than 0.5 wt %, or less than 2 wt %, optionally from 0 to 5 wt %, from 0.1 to 5 wt % or from 0.5 to 2 wt %.

If the alkylate composition further comprises a triamylphenol, e.g., 2,4,6-tri-tert-amylphenol, it optionally comprises the triamylphenol in an amount less than 4 wt %, e.g., less than 2 wt %, less than 1 wt %, less than 0.5 wt %, or less than 1 wt %, optionally from 0 to 5 wt %, from 0.1 to 5 wt % or from 0.5 to 2 wt %. Although low levels of triamylphenols are generally preferred, because 2,4,6-triamylphenol is not a restricted material in some countries, there typically is no need to remove 2,4,6-triamylphenol prior to reacting the alkylate composition with a phosphorous halide to form a phosphite composition. Thus, costly and time-consuming separation processes, e.g., distillation, can be advantageously avoided.

In one aspect, the alkylation process produces and alkylate composition that is substantially colorless, e.g., completely colorless. Colored impurities are undesirable because color generated in the alkylate can be carried through into the final phosphite composition. In one embodiment, the alkylate composition has an American Public Health Association "APHA" color value of less than 100, e.g., less than 75, less than 50, or less than 25, as measured under ASTM D1209. In such aspects where minimal or no colored impurities are present in the alkylate, additional separation processes, e.g., distillation, can be avoided.

Formation of the Alkylate Compositions

The alkylate composition may be formed by contacting one or more phenolics with one or more olefins in the presence of a catalyst and under conditions effective to form the alkylate composition. The one or more olefins preferably contain from 1 to 18 carbons, e.g., from 1 to 8 carbons, or from 4 to 6 carbons. Preferably, the olefin comprises an amylene. As an alternative to using an olefin alkylating agent, one or more alkyl halides, alcohols, MTBE or TAME may be employed. The alkylating agent that is employed may comprise or be derived from a hydrocarbon stream comprising alkanes and alkenes, such as a petrochemical raffinate stream from a $C_4$ or $C_5$ fraction, preferably a $C_5$ fraction, or a dehydrogenation reaction product of an alkane, e.g., isobutane or isopentane. In this aspect, the alkanes pass through the alkylating process unaltered and may be easily separated from the product alkylate composition.

In one embodiment, the ratio of phenol to olefin, e.g., isoamylene, preferably is such that the resulting alkylate composition is suitable for conversion to the desired phosphite composition, e.g., amylaryl phosphite composition, when reacted with a phosphorous halide. In some exemplary embodiments, the olefin, e.g., amylene, to phenolic compound mole ratio ranges from 1:1 to 6:1, e.g., from 1.1:1 to 2:1 or from 1.25:1 to 1.4:1, although these ratios may very somewhat depending, for example, on the catalyst employed in the alkylation process and the desired composition and viscosity for the ultimately formed phosphite composition.

In addition, the composition of phenols, e.g., amylphenols, may be selected and/or adjusted so as to produce a desired liquid phosphite composition having a target viscosity and/or a target stability level. Of course, other factors, e.g., phenolic excess, reaction temperature profile, final residual phenolic content, choice of catalyst, etc., can also affect the resultant phosphite compositions.

As discussed above, in a preferred embodiment, the ratio of monoamyl phenol, e.g., 4-tert-amylphenol, to diamyl phenol, e.g., 2,4-di-tert-amylphenol, in the alkylate compositions ranges from 5:1 to 1:2, e.g., from 5:1 to 1:1.5, from 3:1 to 1:1, or from 1.5:1 to 1:1, and the ratio of phenolics to olefins is preferably selected to yield an alkylate composition suitable for forming phosphite compositions having such compositions.

Although conditions for the alkylation process may vary widely, in some preferred embodiments, the reaction of the phenol and the olefin may occur in an inert atmosphere (e.g., under nitrogen) at an internal temperature of from 60 to 200° C., e.g., from 70 to 145° C. or from 80 to 140° C. The reaction is preferably performed at a pressure of from 0.2 to 10 atm, e.g., from 0.2 to 5 atm or from 0.2 to 4 atm. In a batch reaction, the reaction time may last from 1 to 12 hours, e.g., from 2 to 10 hours, or from 3 to 5 hours. In a continuous reaction, the residence time may be from 0.1 to 5 hours, e.g., from 0.2 to 4 hours or from 0.5 to 1 hour. The alkylation preferably is performed in the presence of a catalyst. The catalyst may, for example, be selected from the group consisting of acid clay catalyst, cationic ion exchange resins, Brönsted acids, e.g., sulfuric acid, Trifluoromethanesulfonic acid (triflic acid) and phosphotungstic acid, or Lewis acids, e.g., $BF_3$ Suitable commercial acid clay catalysts include Fulcat™ 22B (Rockwood Additives). In one embodiment, the sulfonic acid-type cation-exchange resin catalyst useful in the present invention can be, for example, a sulfonated styrene-divinyl benzene copolymer, a sulfonated crosslinked styrene polymer, a phenol formaldehyde-sulfonic acid resin, or a benzene formaldehyde-sulfonic acid resin. Cation exchange resins useful in the present invention include for example styrene-divinylbenzene types of strong acid ion exchange resins such as Dowex™ 50WX4, Dowex 50WX2, Dowex M-31, Dowex Monosphere M-31, Dowex DR-2030 and Dowex Monosphere DR-2030 catalysts (Dow Chemical). Other appropriate resins include: Amberlyst™ 15, Amberlyst 131, Amberlyst 35, Amberlyst 36, and A21 (Rohm and Hass, subsidiary of Dow); Diaion™ WA30, Diaion SK104, Diaion SK1B, Diaion PK208, Diaion PK212 and Diaion PK216 (Mitsubishi); Tulsion™ T-38, Tulsion T-62, Tulsion T-66, Tulsion T-3825 and Tulsion T-3830 (Thermax); Lewatit™ K1131, Lewatit K1221, Lewatit K1261 and Lewatit SC 104 (Sybron Chemicals); Indion™ 180 and Indion 225 (Ion Exchange (India) Limited); and Purolite™ CT-175, Purolite™ CT-169, and Purolite™ CT-275(Purolite). Dowex DR2030 and Fulcat 22B are preferred.

When Dowex DR2030 is utilized, the internal reaction temperature may range from 60° C. to 140° C., e.g., from 80° C. to 120° C., or from 80° C. to 100° C. When Fulcat 22B is utilized, the internal reaction temperature may range from 100° C. to 200° C., e.g., from 120° C. to 180° C., or from 120° C. to 140° C. Thus, in one embodiment, internal reaction temperatures can be decreased significantly by utilizing the Dowex DR 2030 (or similar) cationic exchange catalysts.

In one embodiment, the catalyst is treated, e.g., washed, before the reaction is conducted. As an example, the catalyst may be washed with phenol or another suitable solvent. Some catalysts may contain unbound acid, which may reduce amylate production. Washing of the catalyst removes such catalyst, thus increasing the efficiency of the catalysis.

It is contemplated that alkyl substitution of the aryl groups may be varied by selection of the catalyst used to alkylate the aryl group. For example, in embodiments where an ortho substitution is desired, a milder catalyst, e.g., aluminum phenate or $BF_3$, is utilized. Alternatively, where a meta substitution is desired, a stronger catalyst, e.g., triflic acid, is utilized.

Thus, in one embodiment, a cationic ion exchange catalyst is utilized to catalyst the alkylation process. In a preferred embodiment, the cationic exchange catalyst contains a low amount of water, e.g., the cationic exchange catalyst is substantially anhydrous containing less than 3 wt % water, less than 1 wt % water or less than 0.5 wt % water. An example of such a catalyst is Dowex DR 2030. The anhydrous cationic exchange catalyst beneficially introduces less water, e.g., substantially no water or no water, into the resulting alkylate composition. In these embodiments, the need to further process, e.g., heating or drying, the alkylate compositions after the reaction is minimized or eliminated.

In one embodiment, the cationic exchange catalyst produces an alkylate composition that is clear, e.g., substantially colorless or colorless. As indicated above, colored impurities in the alkylate composition can be undesirably carried through into the final phosphite composition. Typically, clear and colorless phosphite compositions are desired. Thus, colored phosphite compositions are less desired. By utilizing a catalyst that produces substantially colorless alkylate compositions, additional separation, e.g., filtration or distillation, can be advantageously avoided. Surprisingly an unexpectedly, the anhydrous catalysts, e.g., Dowex DR 2030, form alkylate compositions having little (if any) color, as compared to Fulcat 22B. Specifically, the Dowex DR 2030 catalyst may form alkylate compositions having an APHA color value of less than 100, e.g., less than 75, less than 50, or less than 25, as measured under ASTM D1209, even without distilling or treating the as formed alkylate composition. In contrast, the Fulcat catalyst may form alkylate compositions having color. In these cases, the alkylate composition may require further processing, e.g., distillation, to remove at least a portion of the colored impurities.

In one embodiment, the catalyst has a micro-bead form. For example, the catalyst may comprise particles having dry volume sizes, e.g., diameters, less than 3 mm, e.g., less than 2 mm, or less than 1 mm. As such, micro-bead catalyst may be quickly and effectively removed from the resultant reaction mass. An example of such a catalyst is Dowex DR 2030.

In addition, in some embodiments, the catalyst is effectively recycled. As such, the catalyst may, beneficially, maintain catalytic activity after more than two, e.g., more than three, more than four, or more than five, reactions.

In one embodiment, an acid treated clay is utilized. Acid treated clays may have more than 3 wt %, e.g., more than 5 wt %, or more than 10 wt % water content, optionally from 5-20 wt %, e.g., from 8-14 wt % water content. An example of such a catalyst is Fulcat 22B, which is an acid treated montmorillonite clay. In one embodiment, the water generated by the hydrated catalyst is removed, e.g., distilled or stripped, from the alkylate compositions.

In some embodiments, as indicated above, the reaction of phenols and amylenes produces an alkylate compositions comprising 4-tert-amylphenol and 2,4-di-tert-amylphenol. In addition, the reaction may produce by-products, e.g., products other than 4-tert-amylphenol or 2,4-di-tert-amylphenol. 2-tert-amylphenol, 2,4,6-tri-tert-amylphenol and 2,5-di-tert-amylphenol are examples of such by-products. In one embodiment, the by-products, beneficially, make up less than 5 wt %, e.g., less than 3 wt %, less than 2 wt %, less than 1 wt %, or less than 0.5 wt %, of the alkylate compositions, based on the total weight of alkylphenols in the alkylate composition. In one embodiment, one or more of the by-products are separated, e.g., distilled, from the alkylate compositions. In one embodiment, the catalyst employed impacts the amount of byproducts formed.

In other embodiments, the by-products may be beneficial to the alkylate composition. As an example, the by-product may contribute to the formation of a more diverse phosphite compositions, which may aid to improve liquidity or reduce the viscosity of the resultant phosphite compositions or improve solubility of the resulting phosphite composition in the polymer to be stabilized. As an example, a small amount of mono-ortho-phenol, e.g., from 1-4 wt % or from 2-3 wt %, may aid in reducing the viscosity of the resultant phosphite composition.

In some embodiments, the reaction of phenols and amylenes has a conversion rate (to amylated phenols) of greater than 90%, e.g., greater than 95%, greater than 98%, greater than 99%, or greater than 99.5%. In one embodiment, the amount of residual phenol in the amyl alkylate composition is less than 4 wt %, e.g., less than 2 wt % or less than 1 wt %. These low amounts of residual phenol are significantly less than the amounts of residual phenols in other non-amyl alkylate compositions, e.g., butyl, hexyl, heptyl, or octyl alkylate compositions.

In one embodiment, a batch alkylate synthesis takes place in a pot-type reactor. In another embodiment, the alkylate synthesis is conducted on a continuous basis in a continuous type reactor. In the continuous process, the alkylation reaction is optionally quenched using a polar solvent, water, that forms a liquid phase containing most, if not all, of the catalyst and an organic phase containing the alkylated aryl compound, which may be removed by distillation. In alternative embodiments, the reaction is conducted in a fixed bed reactor. When the continuous process takes place over a fixed bed of solid catalyst, a quenching step may not be necessary.

In one aspect of the process, any free phenolic compounds that are not reacted with the olefin may be removed from the mixture of reaction products through distillation at a temperature, for example, of from 70 to 160° C. and at a pressure of from 1 to 10 mbar.

In some embodiments, a mixed olefin and/or mixed phenolic feedstock may be used to form a more diverse alkylate composition, which may be desired to ultimately form a more diverse phosphite composition. Thus, a mixture of lower alkenes comprising one or more amylenes (e.g., two or more $C_3$-$C_6$ olefins, such as a mixture of butylenes and amylenes) may be reacted with the phenolic compound either in parallel (feed in olefin A and B at the same time) or consecutively (i.e. olefin A is reacted first followed by olefin B). Similarly, in another embodiment, a mixture of phenolics, e.g., hydroxybenzene and m-cresol, may be reacted with an amylenes either in parallel (feed in phenolic A and B at the same time) or consecutively (i.e. phenolic A is reacted first followed by phenolic B). Of course, multiple olefins and multiple phenolics may also be reacted in parallel, consecutively or a combination thereof, to form an even more diverse alkylate composition if desired.

Phosphite Compositions

As indicated above, the novel alkylate compositions can be utilized to form compositions of phosphites that are beneficial as, for example, stabilizers in polymeric compositions. Such compositions may comprise at least two different phosphites of structure (VIII):

(VIII)

wherein $R_4$, $R_5$, and $R_6$ are independently selected amylaryl groups and wherein the phosphite composition is a liquid at ambient conditions. Also as discussed above, the inventive alkylate compositions may be reacted, e.g., reacted with phosphorus trihalides, to form the above-identified phosphite compositions.

The amylphenols in the inventive alkylate compositions are directly related to the substituents of these phosphite compositions. Preferably, the alkylate composition provides the ester moieties, e.g., $OR_4$, $OR_5$, and $OR_6$ of structure (VIII), of the resultant phosphite compositions. In one reaction scheme, the phenols are esterified with a phosphorus trihalide to form the desired phosphite composition. Thus, the structures and features of the phosphite substituents should be similar to the structures of the amylphenols in the inventive alkylate compositions discussed above.

In one embodiment, the aryl moiety present in the compounds of the phosphites is an aromatic moiety of from 6 to 18 carbon atoms, e.g., hydroxybenzene, naphthyl, phenanthryl, anthracyl, biphenyl, terphenyl, o-cresyl, m-cresyl, p-cresyl, xylenyl, and the like, preferably hydroxybenzene.

Since the phosphite composition comprises at least two amylaryl phosphite compounds, for at least some of the phosphite compounds in the phosphite composition, the aryl moiety is substituted with one or more amyl groups, i.e., any $C_5$-containing species, and optionally one or more non-amyl alkyl groups, as discussed above.

As noted above, the phosphite composition comprises at least two different amylaryl phosphite compounds, e.g., at least three different amylaryl phosphite compounds, or at least four different amylaryl phosphite compounds, of structure (VIII). The phosphite composition comprises at least two phosphite compounds that contain a combination of the above-mentioned amylaryl groups, e.g., monoamylaryl groups, diamylaryl groups, and optionally triamylaryl groups or a mixture thereof. As indicated above, in addition to containing at least two different amylaryl phosphite compounds, the phosphite compositions may comprise one or more non-amyl amylaryl phosphite compounds, so long as the overall phosphite composition is liquid at ambient conditions. In the preferred embodiment, the inventive phosphite composition comprises at least two different amylaryl phosphite compounds selected from the group consisting of a tris(diamylaryl)phosphite, a tris(monoamylaryl)phosphite, a bis(diamylaryl)monoamylaryl phosphite, and a bis(monoamylaryl)diamylaryl phosphite.

An exemplary tris(diamylaryl)phosphite corresponds to the following formula:

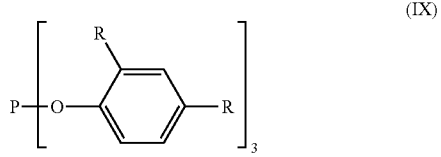

(IX)

wherein each R is a amyl group, the same or different, preferably selected from e.g., n-amyl, t-amyl, iso-amyl or sec-amyl. The amyl groups, R, may differ from one another on a given diamylaryl moiety and/or between adjacent diamylaryl moieties, or a combination thereof.

Although the exemplary tris(diamylaryl)phosphite compound (IX) is uniformly o/p substituted, other substitutions are also possible. For example, in another embodiment, two diamylaryl ester groups on a given phosphite molecule may be o/p substituted, and the third diamylaryl ester group may be o/o substituted. Of course, other combinations are possible. Additionally or alternatively, some tris(diamylaryl) phosphite compounds in the phosphite composition may be uniformly substituted with o/p diamylaryl ester groups, while other tris(diamylaryl)phosphite compounds in the phosphite composition may be uniformly substituted with diamylaryl ester groups that are substituted in different positions, e.g., o/o, or m/m. It is preferred, however, that the majority, e.g., at least 50%, at least 90%, or at least 95% of the diamylaryl ester groups in the overall phosphite composition are o/p-substituted, based on the total number of diamylaryl ester groups in the phosphite composition (i.e., excluding any monoamylated phosphite groups).

The preferred tris(diamylaryl)phosphite species is tris(2,4-di-tert-amylphenyl)phosphite. Thus, the phosphite composition optionally comprises tris(2,4-di-tert-amylphenyl)phosphite in an amount greater than 80 wt. %, greater than 90 wt. % or greater than 95 wt. %, based on the total number of tris(diamylaryl)phosphite species in the phosphite composition. Of course, other tris(diamylaryl)phosphites are also possible.

An exemplary tris(monoamylaryl)phosphite corresponds to the following formula:

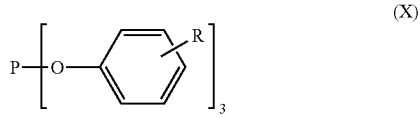

(X)

wherein R may be in the ortho, meta or para position, or a combination thereof, and wherein each R is a amyl group, the same or different from the R on adjacent monoamylaryl ester groups, preferably selected from n-amyl, t-amyl, iso-amyl or sec-amyl.

For the tris(monoamylaryl)phosphites, some monoamylaryl ester groups may be substituted in a manner different from other monoamylaryl ester groups on the same phosphite molecule. For example, one monoamylaryl moiety may be ortho substituted, and an adjacent monoamylaryl moiety on the same molecule may be para substituted. In addition, some tris(monoamylaryl)phosphite molecules may be uniformly monosubstituted in a manner different from other tris(monoamylaryl)phosphite molecules. For example, some tris(monoamylaryl)phosphite molecules may be uniformly para substituted, while other tris(monoamylaryl)phosphite molecules may be uniformly ortho substituted. It is preferred, however, that the majority, e.g., at least 50%, at least 90%, or at least 95%, of the monoamylaryl ester groups are para-substituted, based on the total number of monoamylaryl ester groups (i.e., excluding any polyamylaryl ester groups).

The preferred tris(monoamylaryl)phosphite species is tris(4-tert-amylphenyl)phosphite. Thus, the phosphite composition optionally comprises tris(4-tert-amylphenyl)phosphite in an amount greater than 80 wt. %, greater than 90 wt. % or greater than 95 wt. %, based on the total number of tris(monoamylaryl)phosphite species in the phosphite composition. Of course, other tris(monoamylaryl)phosphites are also possible.

An exemplary bis(diamylaryl)monoamylaryl phosphite corresponds to the following formula:

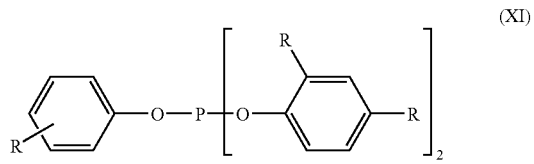

(XI)

wherein R on the monoamylaryl moiety may be in the ortho, meta or para position, or a combination thereof for different bis(diamylaryl)monoamylaryl phosphite compounds in the phosphite composition, and wherein each R is a amyl group, the same or different, preferably selected from n-amyl, t-amyl, iso-amyl and sec-amyl. Although the diamylaryl phosphite moieties in the exemplary bis(diamylaryl)monoamylaryl phosphite compound (XI) above are uniformly o/p substituted, other substitutions are also possible as discussed above in connection with the tris(diamylaryl)phosphite compound (IX).

The preferred bis(diamylaryl)monoamylaryl phosphite is bis(2,4-di-tert-amylphenyl)-4-tert-amylphenyl phosphite, and the phosphite composition preferably comprises bis(2,4-di-tert-amylphenyl)-4-tert-amylphenyl phosphite in an amount greater than 80 wt. %, greater than 90 wt. % or greater than 95 wt. %, based on the total number of bis(diamylaryl)monoamylaryl phosphite species in the phosphite composition. Of course, other bis(diamylaryl)monoamylaryl phosphites are also possible.

An exemplary bis(monoamylaryl)diamylaryl phosphite corresponds to the following formula:

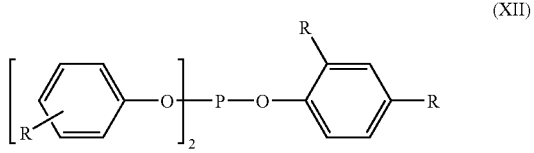

(XII)

wherein R on the monoamylaryl moieties may be in the ortho, meta or para position, or a combination thereof for different bis(monoalkylaryl)dialkylaryl phosphite compounds in the phosphite composition and/or for adjacent monoamylaryl moieties on the same phosphite compound, and wherein each R is a amyl group, the same or different, preferably selected from n-amyl, t-amyl, iso-amyl and sec-amyl. Although the diamylaryl phosphite moiety in the exemplary bis(monoalkylaryl)dialkylaryl phosphite compound (XII) above is o/p substituted, other substitutions are also possible as discussed above.

The preferred bis(monoamylaryl)diamylaryl phosphite is bis(4-tert-amylphenyl)-2,4-di-tert-amylphenyl phosphite, and the phosphite composition preferably comprises bis(4-tert-amylphenyl)-2,4-di-tert-amylphenyl phosphite in an amount greater than 80 wt. %, greater than 90 wt. % or greater than 95 wt. %, based on the total number of bis(monoamylaryl)diamylaryl phosphite species in the phosphite composition. Of course, other bis(monoamylaryl)diamylaryl phosphites are also possible.

Preferably, the phosphite composition comprises at least two different phosphites, e.g., at least three different phosphites, or at least four different phosphites, selected from the group consisting of a tris(diamylaryl)phosphite, a tris(monoamylaryl)phosphite, a bis(diamylaryl)monoamylaryl phosphite, and a bis(monoamylaryl)diamylaryl phosphite. Thus, the phosphite composition comprises at least one phosphite that has at least one aromatic moiety that is multiply substituted, such as a bis(diamylaryl)monoamylaryl phosphite, a bis(monoamylaryl)diamylaryl phosphite or a tris(diamylaryl)phosphite. That is, the phosphite composition does not contain exclusively monosubstituted amylaryl phosphite compounds. In addition to containing multiply-substituted amylaryl phosphite compounds, however, the phosphite composition preferably includes at least one phosphite compound in which each aryl moiety is monosubstituted, e.g., a tris(monoamylaryl)phosphite.

In one aspect, the phosphite composition comprises at least two phosphites selected from the group consisting of tris(4-tert-amylphenyl)phosphite, tris(2,4-di-tert-amylphenyl)phosphite, bis(4-tert-amylphenyl)-2,4-di-tert-amylphenyl phosphite, and bis(2,4-di-tert-amylphenyl)-4-tert-amylphenyl phosphite, wherein the composition is a liquid at ambient conditions. Preferably, the phosphite composition comprises at least two of these compounds, at least three of these compounds or all four of these compounds, in an amount greater than 80 wt. %, 90 wt. % or 95 wt. %, based on the total weight of all phosphites in the phosphite composition. Of course, a minor amount of other species, phosphite or non-phosphite, may be present, e.g., one or more of tris(2-tert-amylphenyl)phosphite, bis(2-tert-amylphenyl)-2,4-di-tert-amylphenyl phosphite, bis(2,4-di-tert-amylphenyl)-2-tert-amylphenyl phosphite and the like.

In one aspect, substantially all of the phosphite compounds in the phosphite composition, e.g., at least 90 wt. %, at least 95 wt. %, or at least 99 wt. % of the phosphite compounds in the phosphite composition, are amylaryl phosphite compounds. Preferably, at least 95%, at least 98% or at least 99% of the aryl moieties are substituted with one or more tert-amyl groups. In addition, at least 95%, at least 98% or at least 99% of the amyl substituents may be tert-amyl substituents.

In some embodiments, the phosphite compositions have an overall phosphorus content that is equal to or greater than TNPP, e.g., at least 4.5 mol %, e.g., at least 4.8 mol %, or at least 5.1 mol %. In terms of ranges, the overall phosphorus content of the phosphite composition may range from 4.5 to 6.0 mol %, e.g., from 4.8 to 5.8 mol %, or from 5.1 to 5.5 mol %, of all phosphorous containing compounds in the phosphite composition.

The relative amounts of the respective phosphite components contained in the phosphite compositions of the invention may vary somewhat so long as the phosphite composition is a liquid at ambient conditions. In terms of ranges, for example, the phosphite composition preferably comprises tris(monoamylaryl)phosphites, e.g., tris(4-tert-amylphenyl)phosphite, in an amount from 20-70 wt %, e.g., from 15-55 wt %, or from 37-54 wt %, and bis(monoamylaryl)diamylaryl phosphites, e.g., bis(4-tert-amylphenyl)-2,4-di-tert-amylphenylphoshite, in an amount from 15-60 wt %, e.g., from 31-50 wt %, or from 34-45 wt %. Optionally, the phosphite composition further comprises tris(diamylaryl)phosphites and/or bis(diamylaryl)monoamylaryl phosphites. If present, the tris(diamylaryl)phosphites, e.g., tris(2,4-di-tert-amylphenyl)phosphite, preferably are present in an amount of from 0-20 wt %, e.g., from 0-5 wt %, or from 0-1 wt %. If present, the bis(diamylaryl)monoamylaryl phosphites, e.g., bis(2,4-di-tert-amylphenyl)-4-tert-amylphenyl phosphite, are preferably present in an amount of from 2-20 wt %, e.g., from 4-20 wt %, or from 5-10 wt %. Unless otherwise indicated, wte % is based on the total weight of all phosphites the composition.

In terms of weight ratios, the phosphite composition optionally has a weight ratio of tris(monoamylaryl)phosphites to the combination of bis(monoamylaryl)diamylaryl phosphites, bis(diamylaryl)monoamylaryl phosphites and tris(diamylaryl)phosphites of from 1:4 to 7:3, e.g., from 2:5 to 3:2, or from 3:5 to 6:5.

The phosphite composition optionally has a weight ratio of bis(monoamylaryl)diamylaryl phosphites to the combination of tris(monoamylaryl)phosphites, bis(diamylaryl)monoamylaryl phosphites and tris(diamylaryl)phosphites of from 1:6 to 3:2 e.g., from 1:3 to 1:1, or from 1:2 to 2:3.

The phosphite composition optionally has a weight ratio of bis(diamylaryl)monoamylaryl phosphites to the combination of tris(monoamylaryl)phosphites, bis(monoamylaryl)diamylaryl phosphites, and tris(diamylaryl)phosphites of from 1:50 to 2:5, e.g., from 1:30 to 1:5, or from 1:20 to 1:9, or optionally less than 0.2:1, less than 0.1:1, less than 0.05:1 or less than 0.02:1.

The phosphite composition optionally has a weight ratio of tris(diamylaryl)phosphites to the combination of bis(monoamylaryl)diamylaryl phosphites, bis(diamylaryl)monoamylaryl phosphites and tris(monoamylaryl)phosphites of from 1:10,000 to 2:5, e.g., from 1:5,000 to 1:20, or from 1:1,000 to 1:100, or optionally less than 0.02:1, less than 0.01:1 or less than 0.005:1.

The viscosity of the phosphite composition may vary depending on the relative amounts of the various phosphite compounds contained therein. In some exemplary embodiments, the phosphite composition has a viscosity less than 11,000 cSt, e.g., less than 7,300 cSt, less than 5,000 cSt, less than 3,000 cSt, or less than 2850 cSt, these viscosities being measured at 30° C. In terms of ranges, viscosity of the composition may range from 1 cSt to 15,000 cSt, from 100 cSt to 12,000 cSt, from 500 cSt to 10,000 cSt, from 500 cSt to 6,500 cSt, from 500 cSt to 5,000 cSt, from 500 cSt to 3,000 cSt, from 1,000 cSt to 4,000 cSt, from 1,500 cSt to 3,500 cSt, from 2,000 cSt to 3,000 cSt, or from 2,000 to 2,800 cSt, these viscosities being measured at 30° C. In one embodiment, the composition has a viscosity less than 5,000 cSt, e.g., less than 3,000 cSt, less than 2,000 cSt, less than 2,000 cSt, or less than 8500 cSt, these viscosities being measured at 40° C. In terms of ranges, viscosity of the composition may range from 1 cSt to 5,000 cSt, from 100 cSt to 5,000 cSt, from 500 cSt to 3,000 cSt, from 500 cSt to 1,500 cSt, or from 750 cSt to 1,150 cSt, these viscosities being measured at 40° C. In one embodiment, the composition has a viscosity less than 1,000 cSt, e.g., less than 500 cSt, less than 385 cSt, less than 255 cSt, less than 240 cSt, or less than 170 cSt, all viscosities being measured at 60° C. In terms of ranges, viscosity of the composition may range from 1 cSt to 1,000 cSt, from 1 cSt to 500 cSt, from 1 cSt to 250 cSt, or from 150 cSt to 250 cSt, all viscosities being measured at 60° C.

In addition, the viscosity of the inventive phosphite compositions may be characterized by the temperature required for the compositions reach a viscosity of 300 cSt (or less). As an example, the inventive phosphite composition may be heated to 50° C. or greater, e.g., 60° C. or greater, or 70° C. or greater, before achieving a viscosity of 300 cSt.

As suggested above, the phosphite compositions of the invention may be characterized based on how the aryl moieties, e.g., phenyl moieties, are substituted, e.g., amyl (e.g., t-amyl) substituted, as a whole. For example, in one embodiment, a majority of the aryl moieties are mono substituted in the para-position, e.g., at least 50%, at least 70%, or at least 90% mono substituted in the para-position, optionally from 50 to 95%, e.g., from 55 to 90 or from 60 to 85% mono substituted in the para-position, based on the number of aryl moieties in the phosphite composition. In other embodiments, some of the aryl moieties are disubstituted, e.g., ortho- and para-disubstituted, at least in part. Preferably at least 10% of the aryl moieties are ortho- and para-disubstituted, e.g., at least 20% ortho- and para-disubstituted, at least 30% ortho- and para-disubstituted, at least 40% ortho- and para-disubstituted, or at least 50% ortho- and para-disubstituted, optionally from 5 to 50% ortho- and para-disubstituted, e.g., from 10 to 45 or from 15 to 40% ortho- and para-disubstituted, based on the total number of aryl moieties in the phosphite composition. In other embodiments, the ratio of monoamylaryl groups to diamylaryl groups ranges from 5:1 to 1:1, e.g., from 4:1 to 1:1, or from 3.5:1 to 2:1.

Depending largely on how the phosphites are manufactured, the phosphite compounds may be similarly substituted with amyl groups on each aryl moiety per molecule. That is, some phosphite compounds may be exclusively monosubstituted, e.g., para-substituted, and/or some phosphite compounds may be exclusively disubstituted, e.g., ortho and para disubstituted, provided that at least some portion of the aryl moieties in the overall phosphite composition are mono-substituted and at least some portion of the aryl moieties in the overall phosphite composition are disubstituted. For example, some or all of the phosphite molecules may contain both mono and disubstituted aryl moieties. Additionally or alternatively, the phosphite composition may comprise phosphite molecules that are exclusively monosubstituted, e.g., para substituted, and/or phosphite molecules that are exclusively disubstituted, e.g., ortho- and para-disubstituted.

As indicated above, the phosphite compositions of the invention include mixed phosphite compounds having aryl moieties that are monoamylated and diamylated. Ideally, few if any of the aryl moieties are trisubstituted. For example, in some embodiments fewer than 3 wt. % of the aryl moieties are trisubstituted, e.g., fewer than 2 wt. %, or fewer than 1 wt. %.

Similarly, it is preferred that few if any of the aryl moieties are monosubstituted in the ortho position. Preferably, the aryl moieties are monosubstituted in the ortho position, if at all, in an amount less than 3 wt. %, e.g., less than 2 wt. % or less than 1 wt. %.

Like the inventive alkylate composition, preferably, the phosphite composition has a low level or is substantially free of phenolics (e.g., phenols, cresols or xylenols), whether alkylated or unalkylated, which is referred to herein as "free phenolics" when contained in the phosphite composition. In terms of amounts, the phosphite composition preferably comprises less than 5 wt. %, less than 3 wt. % or less than 1 wt. %, of free phenolics, based on the total weight of the phosphite composition. Any free phenolics, for example, may be removed by distillation. Extremely low levels of free phenolics may be achieved, for example, by employing a wiped-film molecular (Short-Path) still, wiped film evaporator (WFE), thin film evaporator, or similar equipment. In terms of amounts, the phosphite composition may comprise less than 0.5 wt. %, e.g., less than 0.2 wt. % or less than 0.1 wt. %, of free phenolics, based on the total weight of the phosphite composition.

In other embodiments, a minor amount of free phenolics may be beneficial, for example, as a viscosity reducing agent. Thus, in one embodiment, the phosphite composition comprises a minor amount of free phenolics, e.g., from 1 to 4 weight percent, e.g., from 2 to 3 weight percent, based on the total weight of the phosphite composition.

In addition, the phosphite composition is preferably substantially free of phosphite compounds having unsubstituted aryl moieties, e.g., triphenylphosphites, bis(phenyl)alkylphenyl phosphites or bis(alkylphenyl)phenyl phosphites. In terms of amounts, the phosphite composition preferably comprises less than 3 wt. %, e.g., less than 2 wt %, less than 1 wt. % or less than 0.5 wt. %, phosphite compounds having at least one unsubstituted aryl moiety, based on the total weight of the phosphite composition.

The phosphite composition may be substantially free of phosphite compounds having aryl groups that are substituted with alkyl groups having hydrogens in the α position. That is, in preferred embodiments, at least 95%, at least 98% or at least 99% of the aryl moieties are substituted with alkyl groups having tertiary α-carbons, most preferably tert-amyl.

In some preferred embodiments, the phosphite composition includes one or more hydrolytic stabilizers. Preferred stabilizers include amines of the structure:

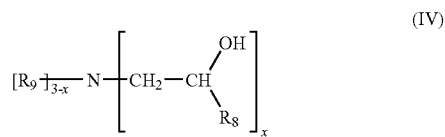

(IV)

wherein x is 1, 2 or 3; $R_8$ is selected from the group consisting of hydrogen, and straight or branched $C_1$-$C_6$ alkyl, and $R_9$ is selected from the group consisting of straight or branched $C_1$-$C_{30}$ alkyl. Preferably $R_8$ is selected from the group consisting of straight or branched $C_1$-$C_4$ alkyl, e.g., methyl or ethyl. Preferably $R_9$ is selected from the group consisting of straight or branched $C_5$-$C_{20}$ alkyl, e.g., straight or branched $C_{10}$-$C_{20}$ alkyl or straight or branched $C_{12}$-$C_{18}$ alkyl. In one embodiment, x is 1 and $R_9$ is straight or branched $C_5$-$C_{20}$ alkyl, e.g., $C_{12}$-$C_{18}$ alkyl. In one embodiment, x is 2 and $R_9$ is straight or branched $C_{10}$-$C_{20}$ alkyl, e.g., $C_{12}$-$C_{18}$ alkyl.

In one aspect the amine is selected from the group consisting of triethanolamine, triisopropanolamine, diethanolamine, diisopropanolamine, and tetraisopropanolethylenediamine.

In another aspect the amine is selected from the group consisting of octyl-bis(2-ethanol)amine, nonyl-bis(2-ethanol)amine, decyl-bis(2-ethanol)amine, undecyl-bis(2-ethanol)amine, dodecyl-bis(2-ethanol)amine, tridecyl-bis(2-ethanol)amine, tetradecyl-bis(2-ethanol)amine, pentadecyl-bis(2-ethanol)amine, hexadecyl-bis(2-ethanol)amine, heptadecyl-bis(2-ethanol)amine, octadecyl-bis(2-ethanol)amine, octyl-bis(2-propanol)amine, nonyl-bis(2-propanol)amine, decyl-bis(2-propanol)amine, undecyl-bis(2-propanol)amine, dodecyl-bis(2-propanol)amine, tridecyl-bis(2-propanol)amine, tetradecyl-bis(2-propanol)amine, pentadecyl-bis(2-propanol)amine, hexadecyl-bis(2-propanol)amine, heptadecyl-bis(2-propanol)amine, octadecyl-bis(2-propanol)amine, and isomers thereof. Commercially available amines include Armostat™ 300 and Armostat 1800 manufactured by Akzo Nobel Polymers.

Additional hydrolytic stabilizers include epoxies such as epoxidized soybean oil (ESBO) commercially available as Drapex™ 39, Drapex 392, Drapex 4.4, and Drapex 6.8 (Chemtura Corp.).

The amine may be present in an amount of from 0.01 to 5 wt. %, e.g., from 0.1 to 1.5 wt. % or from 0.2 to 0.8 wt. %, based on the total weight of the phosphite composition.

Liquid Characteristics

As indicated above, the phosphite composition is a liquid at ambient conditions. As used herein, by "liquid," it is meant that the phosphite composition remains liquid after at least three "freeze/thaw" cycles as opposed to "meta-stable liquids," which do not remain liquid after three or fewer cycles. A freeze/thaw cycle is defined as follows: 1) An ambient temperature composition is stirred for 0.5 hours; 2) The stirred composition is then refrigerated at about 5° C. for three days; and 3) The refrigerated composition is then brought to ambient temperature and held at ambient for 3 days. Upon completion of step 3, the composition is checked for solids content, e.g., crystallization. Completion of steps 1-3 defines one freeze/thaw cycle.

As noted above, the phosphite composition is in liquid physical form at ambient conditions. The prior art teaches several examples of solid phosphite compositions, the components of which are separately solids at ambient conditions, (See JP 59030842; WO 9303092; CA 2,464,551). The present phosphite compositions are, in contrast, liquid at ambient conditions even though the individual components of the compositions would be expected to be solid at the same temperatures. The combination of phosphite components that, individually, would be expected to be solid, when combined in the proper relative amounts, produce phosphite compositions that are liquid at ambient conditions, e.g., they have melting points below 30° C., below 25° C., or below 15° C. As such, the liquid nature of the inventive phosphite compositions is clearly surprising and unexpected.

Processes for Making Phosphite Compositions

The liquid phosphite compositions may be made in the direct reaction of a phosphorus trihalide, e.g., phosphorus trichloride, and two or more amylphenols, e.g., from the above-described novel alkylate compositions. The alkylate compositions may be formed as discussed above.

The inventive alkylate compositions may be reacted with a phosphorus trihalide, with or without catalyst, to form a liquid phosphite composition. The phosphorus trihalide preferably is selected from phosphorus trichloride and phosphorus tribromide. When a catalyst is used, the catalyst may be selected from the group consisting of pyridine, N,N-dimethyldodecylamine, dilauryl methyl amine, trialkylamine, and the hydrochloride salts thereof. The molar ratio of alkylate composition (i.e., alkylated phenol compounds) to phosphorus trihalide preferably is from 3:1 to 5:1, e.g., from 3:1 to 4:1 or from 3.1 to 3.7:1.

The reaction of the alkylated phenols with a phosphorus trihalide may be conducted under an inert atmosphere (e.g., nitrogen) at a temperature of from 5 to 70° C., e.g., from 40 to 70° C. or from 50 to 70° C. The phosphorus trihalide may be charged to the reactor and the alkylate composition may be added thereto. In this case, preferably, the temperature is held at or below 70° C. during the addition of the phosphorus trihalide to the alkylate composition to prevent refluxing the phosphorus trihalide. After the addition of phosphorus trihalide, the temperature is optionally held for 10 minutes to 12 hours, e.g., from 30 minutes to 10 hours, or from 1 hour to 3 hours. The reaction preferably is conducted at a pressure of 0.8 to 4 atm, e.g., from 0.9 to 3 atm or from 1 to 2 atm. Optionally, the alkylate composition may be charged to the reactor and the phosphorus trihalide added thereto. Next, the temperature may be ramped a ramped temperature ranging from 70° C. to 250° C., e.g., from 80° C. to 225° C. or from 90° C. to 200° C. Preferably, the reaction is held at the ramped temperature for from 10 minutes to 12 hours, e.g., from 30 minutes to 10 hours, or from 1 hour to 3 hours. The reaction preferably is conducted at a reduced pressure of 0.01 to 0.5 atm, e.g. from 0.03 to 0.4 atm or from 0.04 to 0.1 atm. During the reaction time, hydrochloric or hydrobromic gas will be evolved, and may be removed by reducing the pressure to about 0.05 atm or sweeping an inert gas such as nitrogen over the reaction mixture. In one aspect the removal of such gases may be performed until the total chloride content in the reaction mixture is less than 50 wppm, e.g., less than 25 wppm or less than 10 wppm.

In one embodiment, a batch alkylate synthesis takes place in a pot-type reactor. In another embodiment, the alkylate synthesis is conducted on a continuous basis in a continuous type reactor. In the continuous process, the alkylation reaction is quenched using a polar solvent, water, that forms a liquid phase containing most, if not all, of the catalyst and a organic phase containing the alkylated aryl compound, which may be removed by distillation. In alternative embodiments, the reaction is conducted in a fixed bed reactor.

In one aspect of the process, any free phenol that is not reacted with the phosphorus trihalide may be liberated by raising the reaction temperature to up to 275° C., e.g., up to 250° C. or up to 225° C., and in a vacuum at a pressure of 0.0001 to 0.1 atm. In one embodiment, a wiped-film molecular (Short-Path) still, wiped film evaporator (WFE), thin film evaporator, or similar equipment may be used to further remove the free cresol or phenol to the very low levels indicated above.

In one embodiment, the step of forming the phosphite composition may occur in one or more neutral solvents. Typical solvents that may be employed include toluene, xylene, methylene chloride, heptane, chloroform, and benzene.

Preferably, the liquid phosphite compositions are obtained in a direct chemical reaction, in which the molar ratio of the alkylated phenolics, e.g., amylated phenolics, is adjusted to yield a phosphite composition that is a liquid at ambient conditions. A schematic of one reaction method that may be employed to form such phosphite compositions is as follows.

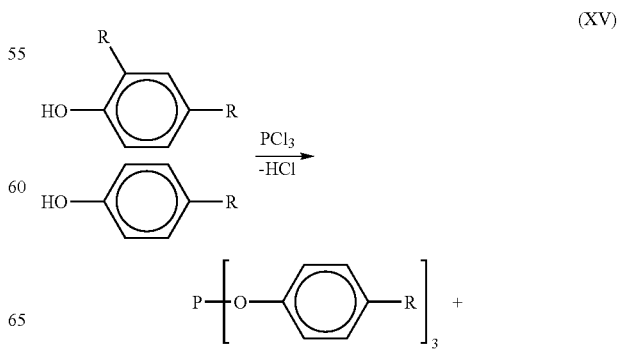

(XV)

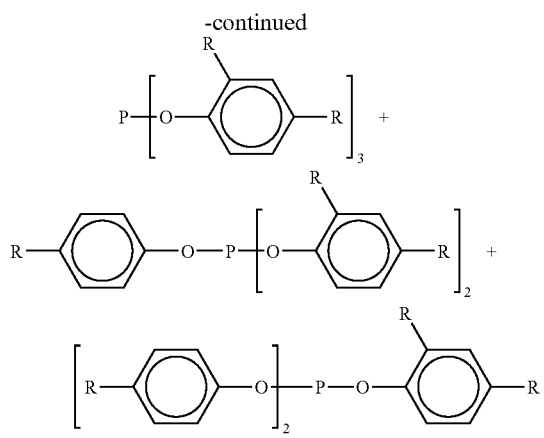

wherein R is independently R₁, R₂, and R₃ as defined above. Note that a minor amount of other alkylated phenolics, e.g., ortho-substituted monoalkylated phenolics, may be included as an additional reactant in the above reaction scheme and would form additional derivative phosphites, but these additional reactants and products have been omitted from Reaction (XV) for clarity.

Stabilizing Composition

As discussed above, a stabilizing amount or effective amount of the phosphite composition of the invention may be used as a secondary antioxidant for various types of polymers. As used herein, by "stabilizing amount" and an "effective amount" it is meant when the polymer composition containing the phosphite compositions of the invention shows improved stability in any of its physical or color properties in comparison to an analogous polymer composition which does not include a phosphite composition of the invention. Examples of improved stability include improved stabilization against, for example, molecular weight degradation, color degradation, and the like from, for example, melt processing, weathering, and/or long term field exposure to air, heat, light, and/or other elements. In one example, improved stability is obtained in the form of one or both of lower initial color as measured by yellowing index (YI) and melt flow rate of the molten polymer or additional resistance to weathering, as measured, for example, by initial yellowing index, or by resistance to yellowing and change in color, when compared to a composition without the stabilizer additive.

The additives and stabilizers described herein are preferably present in an amount effective to improve composition stability. When one of the aforementioned phosphite compositions is utilized, the composition is generally present in an amount from about 0.001 to about 5 wt. %, e.g., from about 0.0025 to about 2 wt. % or from about 0.005 to about 1 wt. %, based on the total weight of the polymer including the weight of the phosphite composition and any other stabilizers or additives. The phosphite compositions of this invention stabilize resins especially during high temperature processing with relatively little change in melt index and/or color, even after multiple extrusions.

The invention further relates to a stabilized thermoplastics, comprising a base polymer (e.g., polymer resin) and any of the aforementioned phosphite compositions of the invention. The polymer may be a polyolefin, and the liquid phosphite composition may be used with a co-stabilizer, for example, hindered phenolics, aromatic amines, hydroxylamines, alkylamine-N-oxides, lactones, and thioethers. Thus, the thermoplastic that is stabilized by the phosphite compositions of the present invention may optionally contain one or more additional stabilizers or mixtures of stabilizers selected from the group consisting of the phenolic antioxidants, hindered amine light stabilizers (HALS), the ultraviolet light absorbers, phosphites, phosphonites, alkaline metal salts of fatty acids, hydrotalcites, metal oxides, epoxydized soybean oils, the hydroxylamines, the tertiary amine oxides, lactones, thermal reaction products of tertiary amine oxides, and the thiosynergists.

In one embodiment, the amount of each component in the stabilizing composition, based on the total weight percent of the polymer or polymeric resin, is shown in Table 1.

TABLE 1

| Component | Range | Preferred Range |
|---|---|---|
| Liquid phosphite compositions | 0.001-5.0 wt % | 0.005-1.0 wt % |
| Primary antioxidant | 0-5.0 wt % | 0.005-2.0 wt % |
| UV or light stabilizers | 0-3.0 wt % | 0.001-2.0 wt % |
| Metal deactivators | 0-3.0 wt % | 0.001-2.0 wt % |
| Other secondary antioxidants | 0-3.0 wt % | 0.001-2.0 wt % |
| Peroxide scavengers | 0-3.0 wt % | 0.001-2.0 wt % |
| Polyamide stabilizers | 0-3.0 wt % | 0.001-2.0 wt % |
| Basic co-stabilizers | 0-3.0 wt % | 0.001-2.0 wt % |
| Nucleating or clarifying agents | 0-3.0 wt % | 0.001-2.0 wt % |
| Aminoxy propanoate | 0-3.0 wt % | 0.001-2.0 wt % |

The phosphite compositions of the invention or the resulting stabilized polymer compositions optionally also comprise primary antioxidants such as the following:

(i) Alkylated monophenols, for example: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2,6-bis(α-methylbenzyl)-4-methylphenol, 2-(α-methylcyclohexyl)-4,6-dimethylphenol, 2,6-dioctadecyl-4-methylphenol, 2,4,6,-tricyclohexyphenol, and 2,6-di-tert-butyl-4-methoxymethylphenol. Commercially available alkylated monophenols include Lowinox™ 624 and Naugard™ 431 made by Chemtura Corp. Other phenols are commercially available such as BHEB.

(ii) Alkylated hydroquinones, for example, 2,6-di-tert-butyl-4-methoxyphenol, 2,5-di-tert-butyl-hydroquinone, 2,5-di-tert-amyl-hydroquinone, and 2,6-diphenyl-4-octadecyloxyphenol. Commercially available alkylated hydroquinones include Lowinox AH25 made by Chemtura.

(iii) Hydroxylated thiodiphenyl ethers, for example, 2,2'-thio-bis-(6-tert-butyl-4-methylphenol), 2,2'-thio-bis-(4-octylphenol), 4,4'-thio-bis-(6-tert-butyl-3-methylphenol), and 4,4'-thio-bis-(6-tert-butyl-2-methyphenol). Commercially available hydroxylated thiodiphenyl ethers include Lowinox TBM6, and Lowinox TBP6 made by Chemtura.

(iv) Alkylidene-bisphenols, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(α-methylcyclohexyl)phenol), 2,2'-methylene-bis-(4-methyl-6-cyclohexylphenol), 2,2'-methylene-bis-(6-nonyl-4-methylphenol), 2,2'-methylene-bis-(6-nonyl-4-methylphenol), 2,2'-methylene-bis-(6-(α-methylbenzyl)-4-nonylphenol), 2,2'-methylene-bis-(6-(alpha,alpha-dimethylbenzyl)-4-nonyl-phenol), 2,2'-methylene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenyl)butane, 1,1-bis(2-methyl-4-hydroxy-5-tert-butylphenyl)butane, 2,2'-isobutylidene-bis(4,6-dimethylphenol), 2,6-di-(3-tert-butyl-5-methyl-2-hydroxybenzyl)-4-methylphenol, 1,1,3-tris-(5-tert-butyl-4- hydroxy-2-methylphenyl)butane, 1,1-bis-(5-tert-butyl-4-hydroxy-2-methylphenyl)-3-dodecyl-mercaptobutane, ethyleneglycol-bis-(3,3,-bis-(3'-tert-butyl-4'-hydroxyphenyl)-butyrate)-di-(3-tert-butyl-4-hydroxy-5-methylphenyl)-dicyclopentadiene, and di-(2-(3'-tert-butyl-2'hydroxy-5'methyl-benzyl)-6-tert-butyl-4-methylphenyl) terephthalate. Commercially available alkylidene-bisphenols include Lowinox 22M46, Lowinox WSP, Lowinox 44B25, Naugard 536, Naugawhite™, and Lowinox 22IB46 made by Chemtura.

(v) Benzyl compounds, for example, 1,3,5-tris-(3,5-di-tert-butyl-4-hydroxybenzyl)-2,4,6-trimethylbenzene, bis-(3, 5-di-tert-butyl-4-hydroxybenzyl)sulfide, isooctyl 3,5-di-tert-butyl-4-hydroxybenzyl-mercapto-acetate, bis-(4-tert-butyl-3-hydroxy-2,6-dimethylbenzyl)dithiol-terephthalate, 1,3,5-tris-(3,5-di-tert-butyl-4 hydroxybenzyl)isocyanurate, 1,3,5-tris-(4-tert-butyl-3-hydroxy-2,6-dimethylbenzyl) isocyanurate, 1,3,5-tris(4-t-butyl-3-hydroxy-2,6-dimethylbenzyl)-1,3,5-Triazine-2,4,6-(1H,3H,5H)-trione, dioctadecyl-3,5-di-tert-butyl-4-hydroxybenzyl-phosphonate, calcium salt of monoethyl 3,5-di-tert-butyl-4-hydroxybenzylphosphonate, 1,3,5-tris-(3,5-dicyclohexyl-4-hydroxybenzyl)isocyanurate. Commercially available benzyl compounds include Anox™ IC-14, Anox 330 and Lowinox 1790 made by Chemtura.

(vi) Acylaminophenols, for example, 4-hydroxylauric acid anilide, 4-hydroxy-stearic acid amilide, 2,4-bis-octylmercapto-6-(3,5-tert-butyl-4-hydroxyanilino)-s-triazine, and octyl-N-(3,5-di-tert-butyl-4-hydroxyphenyl)-carbamate.

(vii) Esters of beta-(3,5-di-tert-butyl-4-hydroxyphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethylisocyanurate, thiodiethyleneglycol, di-hydroxyethyl oxalic acid diamide. Such phenols also include tetrakis [methylene {3,5-di-tert-butyl-4-hydroxycinnamate}]methane. Commercially available esters include Anox 20, Anox 1315, Lowinox GP45, Naugalube 38, Naugalube 531, Anox PP18, Naugard PS48 and Naugard XL-1 made by Chemtura.

(viii) Thio esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, dihydroxyethyl oxalic acid diamide. Commercially available thio esters include Naugalube™ 15 and Anox 70 made by Chemtura.

(ix) Amides of beta-(3,5-di-tert-butyl-4-hydroxyphenol)-propionic acid for example, N,N'-di-(3,5-di-tert-butyl-4-hydroxyphenylpropionyl)-hexammethylen-diamine, N,N'-di-(3,5-di-tert-butyl-4-hydroxyphenylpropionyl) trimethylenediamine, N,N'-di-(3,5-di-tert-butyl-4-hydroxyphenylpropionyl)-hydrazine, N,N'-Hexamethylene bis[3-(3,5-di-t-butyl-4-hydroxyphenyl)propionamide, and 1,2-Bis(3,5-di-tert-butyl-4-hydroxyhydrocinnamoyl)hydrazine. Commercially available amides include Lowinox HD98 and Lowinox MD24 made by Chemtura.

(x) Other phenolic antioxidants include the following phenols. Polymeric phenols such as the reaction product of 4-methylphenol with dicyclopentadiene and isobutylene, commercially available as Lowinox CSTL; Chemtura. Alkylidene-poly-phenols, such as 1,3 tris(3-methyl-4-hydroxyl-5-t-butyl-phenyl)-butane (Lowinox CA22; Chemtura). Thio phenols such as 2,6-di-tert-butyl-4-(4,6-bis(octylthio)-1,3,5-triazin-2-ylamino)phenol (Irganox™ 565; Ciba), 4,6-bis(octylthiomethyl)-o-cresol (Irganox 1520; Ciba); 4,6-bis(dodecylthiomethyl)-o-cresol (Irganox 1726; Ciba). Hydroxylamines, such as bis(octadecyl)hydroxylamine (Irgastab™ FS 042; Ciba). Ester phenols include bis[3,3-bis(4-hydroxy-3-tert-butyl phenyl)butanoic acid]glycol ester (Hostanox™ O3; Clariant Chemicals). Still other phenols include 2-[1-(2-hydroxy-3,5-di-tert-pentylphenyl)ethyl]-4,6-di-tert-pentylphenyl acrylate (Sumilizer GS; Sumitomo Chemical).

In one embodiment, the stabilizing composition comprises one phenolic selected from the group consisting of tetrakis-methylene (3,5-di-t-butyl-4-hydroxylhydrocinnamate)methane (Anox 20), 1,3,5-tris(3,5-di-t-butyl-4-hydroxybenzyl) isocyanurate (Anox IC-14), 1,3,5-tris(4-tert.-butyl-3-hydroxy-2,6-dimethylbenzyl)-1,3,5-triazine-2,4,6-(1H,3H, 5H)-trione (Lowinox 1790), octyl-3-(3,5-di-t-butyl-4-hydroxyphenyl) propionate (Anox PP18), bis(octadecyl) hydroxylamine (Irgastab FS-042), 1,3,5-trimethyl-2,4,6-tris (3,5-di-tert-4-hydroxybenzyl)benzene (Anox 330), 2,6-bis (α-methylbenzyl)-4-methylphenol (Naugalube 431), 3,5-bis (1,1-dimethylethyl)-4-hydroxy-benzenepropanoic acid (Anox 1315), 2,6-di-t-butyl-4-ethyl-phenol (BHEB), and mixtures thereof, and the liquid phosphite composition defined herein.

The phosphite compositions and/or the resulting stabilized polymeric compositions optionally also comprise one or more UV absorbers and/or light stabilizers, such as the following:

(i) 2-(2'-hydroxyphenyl)-benzotriazoles, for example, the 5'-methyl-, 3'5'-di-tert-butyl-, 3'5'-di-tert-amyl-, 5'-tert-butyl-, 5'-tert-amyl-, 5'(1,1,3,3-tetramethylbutyl)-, 5-chloro-3', 5'-di-tert-butyl-, 5-chloro-3'-tert-butyl-5' methyl-, 3'-sec-butyl-5' tert-butyl-,4'-octoxy, 3',5'-ditert-amyl-3',5'-bis-(α,α-dimethylbenzyl)-derivatives. Commercially available 2-(2'-hydroxyphenyl)-benzotriazoles include Lowilite™ 26, Lowilite 27, Lowilite 28, Lowilite 29, Lowilite 35, Lowilite 55, and Lowilite 234 made by Chemtura.

(ii) 2-Hydroxy-benzophenones, for example, the 4-hydroxy, 4-methoxy-, 4-octoxy, 4-decyloxy-, 4-dodecyloxy-, 4-benzyloxy-, 2,4-dihydroxy-, 4,2',4'-trihydroxy- and 2'-hydroxy-4,4'-dimethoxy-derivative. Exemplary 2-hydroxy-benzophenones include 2-hydroxy-4-methoxybenzophenone, 2-hydroxy-4-ethoxybenzophenone, 2,4-dihydroxybenzophenone, and 2-hydroxy-4-propoxybenzophenone. Commercially available 2-(2'-hydroxyphenyl)-benzotriazoles include Lowilite 20, Lowilite 22, Lowilite 20S, and Lowilite 24 made by Chemtura.

(iii) Esters of substituted and unsubstituted benzoic acids for example, phenyl salicylate, 4-tert-butylphenyl-salicilate, octylphenyl salicylate, dibenzoylresorcinol, bis-(4-tert-butylbenzoyl)-resorcinol, benzoylresorcinol, 2,4-di-tert-butyl-phenyl-3,5-di-tert-butyl-4-hydroxybenzoate and hexadecyl-3,5-di-tert-butyl-4-hydroxybenzoate.

(iv) UV absorbers and light stabilizers may also comprise acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methyl-indoline.

(v) Nickel compounds are also suitable UV absorbers and light stabilizers. Exemplary nickel compounds include nickel complexes of 2,2'-thio-bis(4-(1,1,1,3-tetramethylbutyl)-phenol), such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-lauroyl-5-hydroxy-pyrazole, optionally with additional ligands. Commercially available nickel compounds include Lowilite Q84 (2,2'-Thiobis(4-tert-octyl-phenolato))-N-butylamine-Nichel(II) made by Chemtura.

(vi) Sterically hindered amines may be used as UV absorbers and light stabilizers. Sterically hindered amines, for example bis(2,2,6,6-tetramethylpiperidyl)-sebacate, bis-(1,2,2,6,6-pentamethylpiperidyl)-sebacate, n-butyl-3,5-di-tert-butyl-4-hydroxybenzyl malonic acid bis(1,2,2,6,6-pentamethylpiperidyl) ester, condensation product of 1-hydroxyethyl-2,2,6,6-tetramethyl-4-hydroxy-piperidine and succinic acid, condensation product of N,N'-(2,2,6,6-tetramethylpiperidyl)-hexamethylendiamine and 4-tert-octylamino-2,6-dichloro-1,3,5-s-triazine, tris-(2,2,6,6-tetramethylpiperidyl)-nitrilotriacetate, tetrakis-(2,2,6,6-tetramethyl-4-piperidyl)-1,2,3,4-butane-tetra-carbonic acid, 1,1'(1,2-ethanediyl)-bis-(3,3,5,5-tetramethylpiperazinone). Such amines include hydroxylamines derived from hindered amines, such as di(1-hydroxy-2,2,6,6-tetramethylpiperidin-4-yl)sebacate: 1-hydroxy 2,2,6,6-tetramethyl-4-benzoxypiperidine; 1-hydroxy-2,2,6,6-tetramethyl-4-(3,5-di-tert-butyl-4-hydroxy hydrocinnamoyloxy)-piperidine; and N-(1-hydroxy-2,2,6,6-tetramethyl-piperidin-4-yl)-epsiloncaprolactam. Commercially available hindered amines include Lowilite 19, Lowilite 62, Lowilite 77, Lowilite 92 and Lowilite 94 made by Chemtura.

(vii) Oxalic acid diamides, for examples, 4,4'-dioctyloxyoxanilide, 2,2'-di-octyloxy-5',5'-di-tert-butyloxanilide, 2,2'-di-dodecyloxy-5',5'di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'ethyl-5,4-di-tert-butyloxanilide and mixtures of o- and p-methoxy—as well as of o- and p-ethoxy-disubstituted oxanilides.

The polymer resins and phosphite compositions of the invention may also include one or more additional additives, including, for example, one or more of the following:

(i) Metal deactivators, for example, N,N'-diphenyloxalic acid diamide, N-salicylal-N'-salicyloylhydrazine, N,N'-bissalicyloylhydrazine, N,N'-bis-(3,5-di-tert-butyl-4-hydrophenylpropionyl)-hydrazine, salicyloylamino-1,2,4-triazole, bis-benzyliden-oxalic acid dihydrazide.

(ii) Additional secondary antioxidants such as additional phosphites and/or phosphonites, for example, triphenyl phosphite, diphenylalkyl phosphites, phenyldialkyl phosphites, tris(nonyl-phenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite tristearyl sorbitol triphosphite, bis(2,4-dicumylphenyl)pentaerythritol diphosphite, and tetrakis(2,4-di-tert-butylphenyl)4,4'-biphenylene diphosphonite. Commercially available secondary antioxidants include Naugalube TPP, Alkanox™ 240, Ultranox™ 626, Naugard P, Weston™ 399, Weston TNPP, Weston 430, Weston 618F, Weston 619F, Weston DPDP, Weston DPP, Weston PDDP, Weston PTP, Weston TDP, Weston TLP, Weston TPP, and Weston TLTTP (trilauryl trithio phosphite) made by Chemtura; Doverphos™ 4, Doverphos 4-HR, Doverphos 4-HR Plus, Doverphos HiPure 4, and Doverphos S-9228 made by Dover Chemical; and Hostanox PEPQ made by Clariant Chemicals.

(iii) Peroxide scavengers, for example, esters of betathiodipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)-propionate.

(iv) Polyamide stabilizers, for example copper salts in combination with iodides and/or phosphorus compounds and salts of divalent manganese may also be included in the polymer resin and/or phosphite composition.

(v) Basic co-stabilizers, for example, melamine, polyvinylpyrrolidone, dicyandiamide, triallyl cyanurate, urea derivatives, hydrazine derivatives, amines, polyamides, polyurethanes, hydrotalcites, alkali metal salts and alkaline earth metal salts of higher fatty acids, for example, Ca stearate, calcium stearoyl lactate, calcium lactate, Zn stearate, Zn octoate, Mg stearate, Na ricinoleate and K palmirate, antimony pyrocatecholate or zinc pyrocatecholate. Commercially available co-stabilizers include Mark™ 6045, Mark 6045ACM, Mark 6055, Mark 6055ACM, Mark 6087ACM, Mark 6102, Mark CE 345, Mark CE 350, and Mark CE 387, made by Chemtura; and DHT-4A™ made by Kisuma Chemicals.

(vi) Nucleating and clarifying agents, for example, metal salts of 4-tert butylbenzoic acid, adipic acid, diphenylacetic acid, sorbitol and derivatives thereof, sodium benzoate, and benzoic acid.

(vii) Aminoxy propanoate derivatives such as methyl-3-(N,N-dibenzylaminoxy)propanoate; ethyl-3-(N,N-dibenzylaminoxy)propanonoate; 1,6-hexamethylene-bis(3-N,N-dibenzylaminoxy)proponoate); methyl-(2-(methyl)-3-(N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3-(N,N-diethylaminoxy)-propanoate; 3-(N,N-dibenzylaminoxy)propanoic acid potassium salt; and 1,6-hexamethylene bis(3-(N-allyl-N-dodecyl aminoxy)propanoate).

(viii) Other additives, for example, plasticizers, lubricants, emulsifiers, pigments, optical brighteners, flameproofing agents, anti-static agents, blowing agents and thiosynergists such as dilaurythiodipropionate or distearylthiodipropionate.

Optionally the polymer or polymeric resins may include from 5-50 wt %, e.g., 10-40 wt % or 15-30 wt % fillers and reinforcing agents, for example, calcium carbonate, silicates, glass fibers, asbestos, talc, kaolin, mica, barium sulfate, metal oxides and hydroxides, carbon black and graphite.

The invention further pertains to a stabilized polymer, wherein one component comprises a liquid phosphite composition of the present invention and the other a polymer, such as a polyolefin, polyvinyl chloride, etc., or polymeric resins.

The polymer stabilized by such liquid phosphite compositions may be any polymer known in the art, such as polyolefin homopolymers and copolymers, thermoplastics, rubbers, polyesters, polyurethanes, polyalkylene terephthalates, polysulfones, polyimides, polyphenylene ethers, styrenic polymers and copolymers, polycarbonates, acrylic polymers, polyamides, polyacetals, halide-containing polymers, and biodegradable polymers. Mixtures of different polymers, such as polyphenylene ether/styrenic resin blends, polyvinyl chloride/ABS or other impact modified polymers, such as methacrylonitrile and α-methylstyrene containing ABS, and polyester/ABS or polycarbonate/ABS and polyester plus some other impact modifier may also be used. Such polymers are available commercially or may be made by means well known in the art. However, the stabilizer compositions of the invention are particularly useful in thermoplastic polymers, such as polyolefins, polycarbonates, polyesters, polyphenylene ethers and styrenic polymers, due to the extreme temperatures at which thermoplastic polymers are often processed and/or used.

The polymers used in combination with liquid phosphite compositions of the present invention are produced using a variety of polymerization processes including solution, high-pressure, slurry and gas phase using various catalysts including Ziegler-Natta, single-site, metallocene or Phillips-type catalysts. Non-limiting polymers useful with the liquid phosphite compositions include ethylene based polymers such as linear low density polyethylene, elastomers, plastomers, high density polyethylene, substantially linear long chain branched polymers, and low density polyethylene; and propylene based polymers such as polypropylene polymers including atactic, isotactic, and syndiotactic polypropylene polymers, and propylene copolymers such as propylene random, block or impact copolymers.

The polymers, typically ethylene based polymers, have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc, preferably greater than 0.920 g/cc, and most preferably greater than 0.925 g/cc. The polymers produced by the process of the invention typically have a molecular weight distribution, a weight average molecular weight to number average molecular weight (Mw/Mn) of greater than 1.5 to about 15, particularly greater than 2 to about 10, more preferably greater than about 2.2 to less than about 8, even more preferably from about 2.2 to less than 5, and most preferably from 2.5 to 4. The ratio of Mw/Mn can be measured by gel permeation chromatography techniques well known in the art. The polymers of the present invention in one embodiment have a melt index (MI) or (I2) as measured by ASTM-D-1238-E in the range from 0.01 dg/min to 1000 dg/min, more preferably from about 0.01 dg/min to about 100 dg/min, even more preferably from about 0.1 dg/min to about 50 dg/min, and most preferably from about 0.1 dg/min to about 10 dg/min. The polymers of the invention in one embodiment have a melt index ratio (I12/I2) (I21 is measured by ASTM-D-1238-F) of from 10 to less than 25, more preferably from about 15 to less than 25. The polymers of the invention in a preferred embodiment have a melt index ratio (I21/I2) (I21 is measured by ASTM-D-1238-F) of from preferably greater than 25, more preferably greater than 30, even more preferably greater that 40, still even more preferably greater than 50 and most preferably greater than 65.

Polymers used with liquid phosphites compositions of the invention are useful in such forming operations as film, sheet, and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, geomembranes, and pond liners. Molded articles include single and multi-layered constructions in the form of bottles, tanks, large hollow articles, rigid food containers and toys, etc. In addition to the above, the liquid phosphite compositions are used in various rubber based products such as tires, barriers and the like.

In one embodiment, the liquid phosphite compositions are suitable and/or approved for use in polymers, preferably polyolefins, that are used in contact with beverages, foods and other human consumables.

Polymers of monoolefins and diolefins, for example polypropylene, polyisobutylene, polybutene-1, polymethylpentene-1, polyisoprene, or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used. Also useful are copolymers of monoolefins and diolefins with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidene-norbornene; as well as mixtures of such copolymers and their mixtures with polymers mentioned above, for example polypropylene/ethylene propylene-copolymers, LDPE/EVA, LDPE/EAA, LLDPE/EVA, and LLDPE/EAA.

The olefin polymers may be produced by, for example, polymerization of olefins in the presence of Ziegler-Natta catalysts optionally on supports such as, for example, $MgCl_2$, chromium 20 salts and complexes thereof, silica, silica-alumina and the like. The olefin polymers may also be produced utilizing chromium catalysts or single site catalysts, e.g., metallocene catalysts such as, for example, cyclopentadiene complexes of metals such as Ti and Zr. As one skilled in the art would readily appreciate, the polyethylene polymers used herein, e.g., LLDPE, can contain various comonomers such as, for example, 1-butene, 1-hexene and 1-octene comonomers.

The polymer may also include styrenic polymers, such as polystyrene, poly-(p-methylstyrene), 5 poly-(α-methylstyrene), copolymers of styrene or α-methylstyrene with dienes or acrylic derivatives, such as, for example, styrene/butadiene (SBR), styrene/acrylonitrile, styrene/alkyl methacrylate, styrene/maleic anhydride, styrene/maleimide, styrene/butadiene/ethyl acrylate, styrene/acrylonitrile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene (SBS), styrene/isoprene/styrene (SIS), styrene/ethylene/butylene/styrene or styrene/ethylene/propylene/styrene.

Styrenic polymers may additionally or alternatively include graft copolymers of styrene or α-methylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene-propylene-diene terpolymers, styrene and acrylonitrile on polyacrylates or polymethacrylates, styrene and acrylonitrile on acrylate/butadiene copolymers, as well as mixtures thereof with the styrenic copolymers indicated above.

Suitable rubbers include both natural rubber and synthetic rubbers, and combinations thereof. Synthetic rubbers include, but are not limited to, for example, thermoplastic rubbers, ethylene/alpha-olefin/non-conjugated polyene (EPDM) rubbers, ethylene/alpha-olefin (EPR) rubbers, styrene/butadiene rubbers, acrylic rubbers, nitrile rubbers, polyisoprene, polybutadiene, polychloroprene, acrylonitrile/butadiene (NBR) rubbers, polychloroprene rubbers, polybutadiene rubbers, isobutylene-isoprene copolymers, etc. Thermoplastic rubbers include SIS, solution and emulsion SBS, etc.

Nitrile polymers are also useful in the polymer composition of the invention. These include homopolymers and copolymers of acrylonitrile and its analogs, such as polymethacrylonitrile, polyacrylonitrile, acrylonitrile/butadiene polymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be stabilized with the phosphite compositions of the present invention. These include polymers such as polychloroprene, epichlorohydrin homo- and copolymers, polyvinyl chloride, polyvinyl bromide, polyvinyl fluoride, polyvinylidene chloride, chlorinated polyethylene, chlorinated polypropylene, fluorinated polyvinylidene, brominated polyethylene, chlorinated rubber, vinyl chloride-vinyl acetate copolymers, vinyl chloride-ethylene copolymer, vinyl chloride-propylene copolymer, vinyl chloridestyrene copolymer, vinyl chloride-isobutylene copolymer, vinyl chloride-vinylidene chloride copolymer, vinyl chloride-styrene-maleic anhydride terpolymer, vinyl chloride-styrene-acrylonitrile copolymer, vinyl chloride-butadiene copolymer, vinyl chloride isoprene copolymer, vinyl chloride-chlorinated propylene copolymer, vinyl chloride-vinylidene chloride-vinyl acetate terpolymer, vinyl chloride-acrylic acid ester copolymers, vinyl chloride-maleic acid ester copolymers, vinyl chloride-methacrylic acid ester copolymers, vinyl chloride-acrylonitrile copolymer and internally plasticized polyvinyl chloride.

Other useful polymers include homopolymers and copolymers of cyclic ethers, such as polyalkylene glycols, polyethylene oxide, polypropylene oxide or copolymers thereof with bisglycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-2-(2,2,4(4-hydroxyphenyl)-propane) terephthalate and polyhydroxybenzoates as well as block copolyetheresters derived from polyethers having' hydroxyl end groups.

Polyamides and copolyamides which are derived from bisamines and dicarboxylic acids and/or from aminocarboxylic acids or the corresponding lactams, such as polyamide 4, polyamide 6, polyamide 6/6, 6/10, 6/9, 6/12 and 4/6, polyamide 11, polyamide 12, aromatic polyamides obtained by condensation of m-xylene bisamine and adipic acid; polyamides prepared from hexamethylene bisamine and isophthalic or/and terephthalic acid and optionally an elastomer as modifier, for example poly-2,4,4 trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

In another embodiment, the polymer comprises a biodegradable polymer or compostable polymer. Biodegradable polymers are those in which the degradation results from the action of naturally occurring microorganisms, such as bacteria, fungi and algae. Compostable polymers undergoes degradation by biological processes during composting to yield $CO_2$, water, inorganic compounds and a biomass at a rate consistent with other compostable materials. Typically the biodegradable or compostable polymers are derived from plant sources and are synthetically produced. Examples of biodegradable or compostable polymers include poly(glycolic acid) (PGA), poly(lactic acid) (PLA), and co-polymers thereof. Biodegradable or compostable polymers may also be derived from a blend of starch of a plant and a conventional petroleum-based polymer. For example, the biodegradable polymer may be blended with a polyolefin.

Polyolefin, polyalkylene terephthalate, polyphenylene ether and styrenic polymers, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

In one embodiment, the liquid phosphite compositions are added to stabilize natural and synthetic waxes, such as n-paraffin waxes, chloroparaffins, α-olefin waxes, microcrystalline waxes, polyethylene waxes, amide waxes, and Fisher-Tropsch waxes. These waxes may be suitable for making candles.

The instant stabilizers may readily be incorporated into the polymer by conventional techniques at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized compositions of the invention may optionally also contain from about 0.001 to about 5 wt. %, e.g., from about 0.0025 to about 2 wt. % or from about 0.05 to about 0.25 wt. %, of various conventional additives, such as those described previously, or mixtures thereof.

The stabilizers of this invention advantageously assist with the stabilization of polymer compositions especially in high temperature processing against changes in melt index and/or color, even though the polymer may undergo a number of extrusions. The stabilizers of the present invention may readily be incorporated into the polymer compositions by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer.

The compositions of the present invention can be prepared by a variety of methods, such as those involving intimate admixing of the ingredients with any additional materials desired in the formulation. Suitable procedures include solution blending and melt blending. Because of the availability of melt blending equipment in commercial polymer processing facilities, melt processing procedures are generally preferred. Examples of equipment used in such melt compounding methods include: co-rotating and counter-rotating extruders, single screw extruders, disc-pack processors and various other types of extrusion equipment. In some instances, the compounded material exits the extruder through small exit holes in a die and the resulting strands of molten resin are cooled by passing the strands through a water bath. The cooled strands can be chopped into small pellets for packaging and further handling.

All of the ingredients may be added initially to the processing system, or else certain additives may be pre-compounded with each other or with a portion of the polymer or polymeric resin to make a stabilizer concentrate. Moreover, it is also sometimes advantageous to employ at least one vent port to allow venting (either atmospheric or vacuum) of the melt. Those of ordinary skill in the art will be able to adjust blending times and temperatures, as well as component addition location and sequence, without undue additional experimentation.

While the stabilizers of this invention may be conveniently incorporated by conventional techniques into polymers before the fabrication thereof into shaped articles, it is also possible to apply the instant stabilizers by a topical application to the finished articles. Articles may comprise the instant stabilizer compounds and polymers and may be made into, for example, head lamp covers, roofing sheets, telephone covers, aircraft interiors, building interiors, computer and business machine housings, automotive parts, and home appliances. The articles may be made by extrusion, injection molding, roto-molding, compaction, and other methods. This may be particularly useful with fiber applications where the instant stabilizers are applied topically to the fibers, for example, by way of a spin finish during the melt spinning process.

Other Applications

The phosphite compositions may have uses in addition to polymer stabilization. For example, it may be desirable to react the phosphite composition to form a new derivative product, that may of additional uses. Transesterification processes, for example, such as those disclosed in Hechenbleikner et al., U.S. Pat. No. 3,056,823, which is incorporated herein by reference, may also be employed. Specifically, the process described by Hechenbleikner et al. involves transesterifying a triaryl phosphite with a monohydroxy hydrocarbon in the presence of a small but catalytically effective amount of a metal alcoholate or metal phenolate. To avoid contamination, the alcoholate of the particular alcohol to be transesterified is employed. Instead of employing a pre-formed alcoholate, the alcoholate can be formed in situ by adding the metal, e.g., sodium, potassium or lithium to the alcohol prior to adding the triaryl phosphite. The mono alcohol and triaryl phosphite are reacted in the mol ratio of three mols of the alcohol to one mol of the triaryl phosphite.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

EXAMPLES

The present invention will be further understood in view of the following non-limiting examples.

Preparation of Alkylate Compositions (Inventive)

10 g of Dowex DR 2030 was washed three times, each with 50 g of molten phenol. The used phenol was discarded between washes. After the final wash the Dowex DR 2030/phenol slurry was charged to a pre-heated (about 90° C.) jacketed vessel under nitrogen. Additional molten phenol was charged to the vessel such that the total amount used was 207.2 g (2.2 moles). The mixture was heated to about 90° C. and agitation was initiated. 182.5 g (2.6 moles) of 2-methyl-2-butene (isoamylene) was added over 3 hours at a uniform rate and below the surface of the phenol. Once the addition was complete, the reaction was held at about 90° C. to allow for transalkylation. After 3 hours of transalkylation, the reaction mixture was allowed to settle and the amylated phenol was decanted from the Dowex. The un-alkylated phenol and any residual water were removed by vacuum distillation under a pressure of 60 mbar at an internal temperature of 163° C. (vapor temperature of 52° C.). The un-alkylated phenol/water removal was considered complete when the water content was less than 50 ppm and the phenol content was less than 0.5%. The mass of the dried alkylate was 309.2 g. The dried alkylate contain a small amount 2,4,6-tri-tert-butylphenol, thus, further distillation was not necessary.

Analysis of Amylated Phenol Alkylate (Inventive)

TABLE 2

| Gas Chromatograph ("GC") analysis | |
|---|---|
| phenol | 0.4% |
| 2-amylphenol | 0.87% |
| 4-amylphenol | 70.01% |
| 2,4-diamylphenol | 27.05% |
| Impurities | 1.67% (no one impurity was present in amounts greater than 0.12%. |
| $H_2O$ Content | <50 ppm |

Preparation of Amylaryl Phosphite Composition (Inventive)

200 g of molten amylated phenol alkylate was charged to a pre-heated (about 90° C.) jacketed vessel. The alkylate was heated to pre-heated about 90° C. and agitation was initiated. 45.1 g of (0.33 moles) of phosphorus trichloride was added over 3 hours at a uniform rate and below the surface of the amylated phenol. During the addition of the phosphorus trichloride, the temperature was ramped at a uniform rate from about 90° C. to about 150° C. The resultant HCl off-gas was absorbed by a scrubbing unit. Once all the phosphorus trichloride had been added, the reaction mixture was held at 150° C. for 1 hour or until the HCl production had stopped. The reaction mixture was then heated from 150° C. to 200° C. over 1 hour. Once the reaction mixture had reached 200° C., the reaction was degassed by applying a water vacuum (60-80 mbar of pressure). The reaction mixture was degassed until the total chlorine content was less than 25 ppm. Once the total chlorine content had reached this level, the reaction was cooled to about 100° C. The mass of the reaction mixture was 174.5 g. The excess amylated phenol was removed (to less than 1% as measured by GC) by passing the reaction mixture down a KDL1 short path distillation system at the following conditions:

TABLE 3

Distillation Conditions

First Pass

| | |
|---|---|
| Feed Rate | 4 g/min |
| Oil Temperature | 178° C. |
| Vacuum | 0.5 mbar |
| Wiper Speed | 500 rpm |

Second Pass

| | |
|---|---|
| Feed Rate | 5 g/min |
| Oil Temperature | 218° C. |
| Vacuum | 0.5 mbar |
| Wiper Speed | 500 rpm |

The mass of amylaryl phosphite produced was 128.5 g. The mass of the amylated phenol recovered after KDL1 distillation was 32.6 g.

The resultant phosphite product had the following properties.

TABLE 4

Amylaryl Phosphite Properties

| | |
|---|---|
| Physical Form | Clear, colorless liquid; mobile at ambient conditions |
| AN | 0.018 mgKOH/g |
| GC | 0.54 amylated phenols |
| | 99.46% mixed (amylaryl)phosphites |

Several additional alkylate compositions were prepared as indicated in Table 5.

TABLE 5

Alkylate compositions

| | GC % | | | |
|---|---|---|---|---|
| Mixture | Phenol | 2-amylphenol | 4-amylphenol | 2,4-diamylphenol |
| 1 | 0.73 | 0.76 | 79.81 | 17.69 |
| 2 | 0.08 | 1.18 | 77.21 | 20.43 |
| 3 | 0 | 1.01 | 74.13 | 22.29 |
| 4 | 0.08 | 0.94 | 71.41 | 24.05 |
| 5 | 0 | 0.87 | 70.01 | 27.05 |
| 6 | 0 | 0.93 | 67.76 | 29.80 |
| 7 | 0 | 0.56 | 66.52 | 32.01 |
| 8 | 0 | 0.98 | 65.00 | 32.20 |
| 9 | 0 | 0.71 | 62.29 | 34.07 |
| 10 | 0.23 | 1.04 | 59.38 | 37.15 |
| 11 | 0 | 0.82 | 60.90 | 37.20 |
| 12 | 0.14 | 0.74 | 56.77 | 41.50 |
| 13 | 0 | 0.42 | 50.15 | 44.64 |

These alkylate compositions were reacted with phosphorus trichloride to form the corresponding phosphite compositions, as shown in Table 6.

TABLE 6

Amylaryl Phosphite compositions

| Composition | Residual phenol | Tris(4-amyl) phosphite | Di(4-amyl),2,4-diamyl phosphite | 4-amyl, di(2,4-diamyl) phosphite | Tris(2,4-diamyl) Phosphite | Tris(nonylphenyl) phosphite |
|---|---|---|---|---|---|---|
| A | — | | | | | 100 |
| B | — | | | | | 100 |
| 14 | 0.75 | 65.57 | 25.24 | 2.31 | 0 | — |
| 15 | 0.75 | 63.85 | 27.31 | 2.86 | 0 | — |
| 16 | 0 | 57.54 | 31.77 | 4.18 | 0 | — |
| 17 | 0.56 | 50.91 | 29.28 | 3.98 | 0 | — |
| 18 | 0.54 | 54.30 | 34.16 | 5.37 | 0 | — |
| 19 | 0 | 47.79 | 36.06 | 6.59 | 0 | — |
| 20 | 1.04 | 46.70 | 36.00 | 7.64 | 0 | — |
| 21 | 0.69 | 46.25 | 37.92 | 7.44 | 0 | — |
| 22 | 0.20 | 42.57 | 39.59 | 8.53 | 0 | — |
| 23 | 0.68 | 37.70 | 40.38 | 9.77 | 0.68 | — |
| 24 | 0.55 | 37.72 | 42.60 | 11.92 | 0.75 | — |
| 25 | 0.74 | 33.55 | 44.29 | 14.78 | 1.07 | — |
| 26 | 0.50 | 21.87 | 44.07 | 19.6 | 1.90 | — |

The viscosities of the phosphite compositions were measured at 30° C., 40° C., and 60° C. The results are shown in Table 7.

TABLE 7

Viscosities of Amylaryl Phosphite compositions, cSt

| Composition | 30° C. | 40° C. | 60° C. |
|---|---|---|---|
| A | 3182 | 1237 | 242 |
| B | 3678 | 1295 | 258 |
| 14 | 2298 | 879 | — |
| 15 | 2589 | 819 | 160 |
| 16 | 2846 | 1046 | — |
| 17 | 3271 | 1051 | — |
| 18 | 3168 | 1159 | — |
| 19 | 3630 | 1144 | — |
| 20 | 3905 | 1000 | — |
| 21 | 4054 | 1232 | — |
| 22 | 4320 | 1328 | — |

TABLE 7-continued

Viscosities of Amylaryl Phosphite compositions, cSt

| Composition | 30° C. | 40° C. | 60° C. |
|---|---|---|---|
| 23 | 4958 | 1487 | — |
| 24 | 5357 | 1552 | 250 |
| 25 | 6422 | 1825 | — |
| 26 | 10808 | 3054 | 385 |

Preparation of Butylate Composition (Comparative)

16.8 g of Dowex DR 2030 was washed three times, each with 50 g of molten phenol. The used phenol was discarded between washes. After the final wash the Dowex DR 2030/phenol slurry was charged to a pre-heated (about 90° C.) jacketed vessel under nitrogen. Additional molten phenol was charged to the vessel such that the total amount used was 338.2 g (3.59 moles). The mixture was heated to about 90° C. and agitation was initiated. 244.0 g (4.35 moles) of 2-methylpropene (butene) was added over 3 hours at a uniform rate and below the surface of the phenol using a sintered frit. Once the addition was complete, the reaction was held at about 90° C. to allow for transalkylation. After 3 hours of transalkylation, the reaction mixture was allowed to settle and the butylated phenol was decanted from the Dowex. 567.5 g of crude butylated phenol was obtained. 435 g of the crude butylated phenol were charged to a vacuum fractional distillation unit. The un-alkylated phenol and any residual water were removed by vacuum distillation under a pressure of 26 in Hg at an internal temperature of 138° C. (vapor temperature of 60° C.). The un-alkylated phenol/water removal was considered complete when the water content was less than 50 ppm and the phenol content was less than 0.5%. The mass of the dried alkylate was 309.2 g. To separate any undesired impurities, e.g., tri-butylphenol, 2,4,6-tri-tert-butylphenol, from the main fraction, which contains 4-tert-butylphenol and 2,4,-di-tert-butylphenol, the main fraction was then distilled under a vacuum at 26 in Hg at an internal temperature of 143° C. (vapor temperature of 128° C.) until an internal temperature of 145° C. (vapor temperature of 136° C.) was reached. The mass of the dried alkylate was 395.5 g.

Analysis of Butylated Phenol Alkylate (Comparative)

TABLE 8

Gas Chromatograph ("GC") analysis

| | |
|---|---|
| phenol | 0.00% |
| 2-tert-butylphenol | 1.23% |
| 4-tert-butylphenol | 78.06% |
| 2,4-di-tert-butylphenol | 19.70% |
| 2,4,6-tri-tert-butylphenol | 0.00% |
| Impurities | 1.01% (no one impurity was present in amounts greater than 0.12%. |
| $H_2O$ Content | <50 ppm |

Preparation of Butylaryl Phosphite Composition (Comparative)

335 g (2.08 moles) of molten butylated phenol alkylate was charged to a pre-heated (about 90° C.) jacketed vessel under nitrogen. The alkylate was heated to pre-heated about 90° C. and agitation was initiated. 90.3 g of (0.66 moles) of phosphorus trichloride was added over 3 hours at a uniform rate and below the surface of the amylated phenol. During the addition of the phosphorus trichloride, the temperature was ramped at a uniform rate from about 90° C. to about 150° C. The resultant HCl off-gas was absorbed by a scrubbing unit. Once all the phosphorus trichloride had been added, the reaction mixture was held at 150° C. for 1 hour or until the HCl production had stopped. The reaction mixture was then heated from 150° C. to 200° C. over 1 hour. Once the reaction mixture had reached 200° C., the reaction was degassed by applying a water vacuum (60-80 mbar of pressure). The reaction mixture was degassed until the total chlorine content was less than 25 ppm. Once the total chlorine content had reached this level, the reaction was cooled to about 100° C. The mass of the crude reaction mixture was 346.0 g. The excess butylated phenol was removed (to less than 1% as measured by GC) by distillation under a pressure of 1 mbar up to an internal temperature of 253° C. (vapor temperature 130° C.). The mass of butylaryl phosphite produced was 318.2 g. The mass of the amylated phenol recovered after distillation was 27.7 g.

Additional butylated phenol compositions were prepared as indicated in Table 9. The butylated phenol compositions were prepared as indicated above, or by preparing a binary composition of 4-tert-butylphenol and 2,4-di-tert-butylphenol.

TABLE 9

Butylate Compositions

| | GC % | | | |
|---|---|---|---|---|
| Mixture | Phenol | 2-tert-butylphenol | 4-tert-butylphenol | 2,4-di-tert-butylphenol |
| Butylate | | | | |
| 27 | 0.94 | 3.20 | 76.55 | 18.90 |
| 28 | 0 | 1.23 | 78.06 | 19.70 |
| 29 | 0.34 | 1.34 | 84.9 | 13.10 |
| 30 | 0 | 1.39 | 84.45 | 13.06 |
| Binary | | | | |
| 31 | 0 | 0 | 75.00 | 25.00 |
| 32 | 0 | 0 | 80.00 | 20.00 |
| 33 | 0 | 0 | 66.70 | 33.30 |

These butylate mixtures were reacted with phosphorus trichloride to form phosphite compositions, having the viscosities shown in Table 10, wherein Mixtures 27-30 correspond to Mixtures 34-37 and Mixtures 31-33 correspond to Mixtures 38-40.

TABLE 10

Butylaryl Phosphite compositions

| | Viscosity, cSt | | | | |
|---|---|---|---|---|---|
| Composition | 30° C. | 40° C. | 50° C. | 60° C. | Stability |
| C* | 3,182 | 1,237 | — | 242 | — |
| D* | 3,678 | 1,295 | — | 258 | — |
| 34 | 12,797 | 2,240 | — | 233 | Y |
| 35 | 20,544 | 3,186 | — | 270 | Y |
| 36 | 9,629 | 1,719 | — | 196 | N |
| 37 | 7,481 | 3,198 | 812 | — | — |
| 38 | 45,292 | 4,757 | 1,123 | 405 | — |
| 39 | 15,925 | 4,140 | 949 | — | — |
| 40 | — | 10,486 | 1,853 | — | — |

*Compositions C and D are TNPP.

As shown in Table 7, Compositions 14-26, which were prepared using the inventive alkylate compositions, are liquids and exhibit low viscosities, in most cases, well below 10,000 cSt, e.g., below 7,000 cSt. These liquids remained liquid after three thaw cycles. This result is clearly surprising and unexpected based on the high viscosity or solid nature of the individual components of the compositions. To the contrary, one of ordinary skill in the art would expect a composition of the individual amylaryl phosphites to have a high viscosity or to be solid in form.

In addition, as shown in Table 10, comparative compositions 34-40, which do not utilize the inventive alkylate compositions and instead utilize butylate mixtures, exhibit high viscosities, e.g., above 7,000 cSt, in most cases, over 12,000 cSt. Thus, phosphite compositions 14-26 demonstrate significantly lower viscosities and also maintain liquid stability, i.e., the compositions are not meta-stable. As such, these compositions are much more easily incorporated into polymeric compositions, e.g., polymeric resins. This result is clearly surprising and unexpected based on the fact that similar alkylaryl substituted phosphites demonstrate significantly higher viscosities.

Also, compositions 14-16, which were prepared using the inventive alkylate compositions, exhibit viscosities ranging from 2298 cSt to 2846 cSt, which are significantly less than the viscosity for tris(nonylphenyl)phosphite ("TNPP"), which ranges from 3182 to 3678. Such significant reductions in viscosity over similarly substituted phosphites, e.g., tris(nonylphenyl)phosphite, are clearly surprising and unexpected.

The significantly lower viscosities, as demonstrated above, allow for the phosphite compositions prepared from the inventive alkylate compositions to be more easily incorporated into the respective polymer compositions without further processing steps, e.g., heating or melting.

In addition, the data presented in Tables 6 and 7 demonstrate the ability to control the viscosity of the phosphite composition by adjusting the composition of the alkylate compositions. In addition, the amount of residual phenolic in the alkylate compositions can also be adjusted to control the viscosity of the resultant phosphite composition.

Comparison of Inventive Phosphite Compositions to TNPP

Polymeric compositions were prepared by combining various phosphite stabilizer compositions with a Linear Low Density Polyethylene ("LLDPE") resin, a zinc stearate acid scavenger ("ZnSt"), and an additional stabilizer, Anox PP18® from Chemtura Corporation. In each case, the phosphite stabilizer was added in an amount sufficient to achieve a pure phosphite content of 17 ppm. TNPP was added to the Reference composition and a amlphenyl phosphite composition prepared using an alkylate compositions of the invention was added to Composition 41. Table 11 shows the components of the polymeric compositions.

TABLE 11

Polymeric Compositions

|  | Reference (TNPP) | 41 |
| --- | --- | --- |
| LLDPE | 99.89 | 99.8965 |
| ZnSt | 0.05 | 0.05 |
| Anox PP18 | 0.02 | 0.02 |
| TNPP | 0.04 | — |
| Amylphenyl phosphite composition | — | 0.0335 |

These polymeric compositions were tested for Melt Flow Index ("MFI"), Yellowing Index ("YI"), and Gas Fading ("GF").

TABLE 12

MFI Results

|  | Pass 0 | Pass 1 | Pass 3 | Pass 5 |
| --- | --- | --- | --- | --- |
|  | MFI at 2.16 kg during multiple passes at 230° C., g/10 min. | | | |
| Reference | 0.967 | 0.904 | 0.778 | 0.637 |
| Composition 41 | 0.956 | 0.924 | 0.788 | 0.618 |
|  | MFI at 21.6 kg during multiple passes at 230° C., g/10 min | | | |
| Reference | 23.027 | 23.066 | 21.614 | 20.973 |
| Composition 41 | 22.673 | 23.001 | 21.691 | 20.647 |

MFI is a measurement of melt flow. High melt flow is preferred, thus, minimizing reduction of melt flow over multiple passes is desirable. As shown in Table 12, at 2.16 kg, the reference composition (with TNPP) showed a Pass 0 MFI of 0.967 g/10 min. and a Pass 5 MFI of 0.637 g/10 min., which is a difference of 0.330 g/10 min. Composition 41 showed a Pass 0 MFI of 0.956 g/10 min. and a Pass 5 MFI of 0.618 g/10 min., which is a difference of 0.338 g/10 min. At 21.6 kg, the reference composition showed a Pass 0 MFI of 23.027 g/10 min. and a Pass 5 MFI of 20.973 g/10 min., which is a difference of 2.054 g/10 min. Composition 41 showed a Pass 0 MFI of 22.673 g/10 min. and a Pass 5 MFI of 20.647 g/10 min., which is a difference of 2.026 g/10 min. Thus, the melt flow retention of Composition 41 was quite similar to that of the reference composition.

TABLE 13

YI Results

|  | YI during multiple passes at 230° C., g/10 min | | | |
| --- | --- | --- | --- | --- |
|  | Pass 0 | Pass 1 | Pass 3 | Pass 5 |
| Reference | −1.249 | 0.600 | 0.718 | 1.203 |
| Composition 41 | −1.191 | 0.179 | 0.389 | 0.578 |

YI is a measurement of the degree of color of a polymeric composition. A low YI is desirable. As shown in Table 13, the YI values for Composition 41 are similar to or less than the YI values for the reference composition.

TABLE 14

GF Results

|  | GF, after hours of $NO_x$ exposure | | | | |
| --- | --- | --- | --- | --- | --- |
|  | 2 | 25 | 94 | 120 | 140 |
| Reference | 3.26 | 6.27 | 9.34 | 10.11 | 10.52 |
| Composition 41 | 2.49 | 7.90 | 8.97 | 9.61 | — |

GF is a measurement of the degree of color of a polymeric composition with exposure to $NO_x$ gas. Again, a low GF is desirable. As shown in Table 14, the GF values for Composition 41 are similar to or less than the GF values for the reference composition.

As stated above, the phosphite compositions produced using the inventive alkylate compositions, clearly demonstrate the ability to stabilize polymeric compositions as effectively or more effectively than TNPP. As noted above, however, these phosphite compositions do not present estrogenicity concerns.

In view of the many changes and modifications that can be made without departing from principles underlying the invention, reference should be made to the appended claims for an understanding of the scope of the protection to be afforded the invention.

What is claimed is:

1. A method for forming a phosphite composition which phosphite composition is a liquid at ambient conditions and comprises at least two of a tris(diamylaryl)phosphite; a tris(monoamylaryl)phosphite; a bis(diamylaryl)monoamylaryl phosphite; and a bis(monoamylaryl)diamylaryl phosphite, the method comprising: contacting one or more amylenes with a phenol at a molar ratio ranging from 1:1 to 6:1 in the presence of a catalyst and under conditions effective to form an alkylate composition comprising
   a monoamylphenol in an amount ranging from 25 weight percent to 99 weight percent; and
   a diamylphenol in an amount ranging from 1 weight percent to 60 weight percent;
   wherein the weight percentages are based on the total weight of all components in the alkylate composition; and
   reacting a phosphorus polyhalide with the alkylate composition to produce the phosphite composition.

2. The method according to claim 1, wherein the ratio of monoamylphenol to diamylphenol in the alkylate composition ranges from 5:1 to 1:2.

3. The method according to claim 1, wherein at least 50 weight percent of the monoamylphenol in the alkylate composition is substituted with amyl groups in the para-position.

4. The method according to claim 1, wherein at least 10 weight percent of the diamylphenol in the alkylate composition is substituted with amyl groups in the ortho-position and the para-position.

5. The method according to claim 1, wherein the monoamylphenols and diamylphenols combined are present in an amount greater than 90 weight percent, based on the total amount of all phenols in the alkylate composition.

6. The method according to claim 1, wherein at least 90 weight percent of the amyl groups are tert-amyl.

7. The method according to claim 6, wherein the monoamylphenol in the alkylate composition is 4-tert-amylphenol and the diamylphenol in the alkylate composition is 2,4-di-tert-amylphenol.

8. The method according to claim 7, wherein the 4-tert-amylphenol is present in an amount ranging from 45 weight percent to 80 weight percent and the 2,4-di-tert-amylphenol is present in an amount ranging from 10 weight percent to 50 weight percent.

9. The method according to claim 1, wherein the alkylate composition contains less than 4 weight percent tri-alkylaryl compounds.

10. The method of claim 1, wherein the catalyst used when contacting one or more amylenes with a phenol is selected from the group consisting of Bronsted acids and Lewis acids.

11. The method of claim 1, wherein the catalyst is selected from the group consisting of acid clay catalysts, cationic ion exchange resins, sulfuric acid, nitric acid, $BF_3$, trifluoromethanesulfonic acid and phosphotungstic acid.

12. The method of claim 1, wherein the catalyst used when contacting one or more amylenes with a phenol is anhydrous.

13. The method of claim 1, wherein the contacting of one or more amylenes with a phenol occurs at internal temperatures ranging from 60° C. to 200° C. and pressures ranging from 0.2 atmospheres to 10 atmospheres.

* * * * *